United States Patent [19]
Blank

[11] Patent Number: 5,913,826
[45] Date of Patent: Jun. 22, 1999

[54] WIDEBAND EXTERNAL PULSE CARDIAC MONITOR

[75] Inventor: Seymour Blank, New York, N.Y.

[73] Assignee: K-One Technologies, New York, N.Y.

[21] Appl. No.: 08/661,910

[22] Filed: Jun. 12, 1996

[51] Int. Cl.$^6$ .................................................. A61B 05/00
[52] U.S. Cl. ........................ 600/500; 600/504; 600/547
[58] Field of Search ............................. 600/485, 493–6, 600/500–507, 526, 450, 547

[56] References Cited

U.S. PATENT DOCUMENTS

| | | | |
|---|---|---|---|
| 4,074,711 | 2/1978 | Link et al. | 128/2.05 A |
| 4,349,034 | 9/1982 | Ramsey, III | 128/681 |
| 4,389,580 | 6/1983 | Bendyshe Walton et al. | 307/400 |
| 4,625,277 | 11/1986 | Pearce et al. | 364/416 |
| 4,718,428 | 1/1988 | Russell | 128/679 |
| 4,793,360 | 12/1988 | Miyawaki et al. | 128/681 |
| 4,796,184 | 1/1989 | Bahr et al. | 364/413.03 |
| 4,981,141 | 1/1991 | Segalowitz | 128/696 |
| 5,178,154 | 1/1993 | Ackmann et al. | 128/713 |
| 5,188,106 | 2/1993 | Nappholz et al. | 128/419 PG |
| 5,211,177 | 5/1993 | Chesney et al. | 128/672 |
| 5,222,020 | 6/1993 | Takeda | 364/413.03 |
| 5,241,966 | 9/1993 | Finkelstein et al. | 128/713 |
| 5,253,329 | 10/1993 | Villarreal et al. | 395/24 |
| 5,265,615 | 11/1993 | Frank et al. | 128/672 |

(List continued on next page.)

FOREIGN PATENT DOCUMENTS

| | | |
|---|---|---|
| A208520 | 7/1986 | European Pat. Off. . |
| A249243 | 6/1987 | European Pat. Off. . |
| A353315 | 8/1988 | European Pat. Off. . |
| A353316 | 8/1988 | European Pat. Off. . |
| A379996 | 1/1990 | European Pat. Off. . |

OTHER PUBLICATIONS

Blank, S.G., "*The Korotkoff Signal and its Relationship to Arterial Pressure Pulse*", Cornell University (1987) (UMI 8810638).

Blank, et al, *Association of the Auscultatory Gap*, Ann Intern Med 124 (10): 877–883 (May 1996).

Blank, et al. *Isolated Elevation of Diastolic Blood Pressure*, Hypertension 26(3): 383–389 (Sep. 1995).

Blank, et al, *How Should Diastolic Blood Pressure be Defined*, Hypertension 24(2): 234–240 (Aug. 1994).

Blank, et al, *Characterization of Auscultatory Gaps*, Hypertension 17(2): 225–233 (Feb. 1991).

Blank, et al, *Wideband External Pulse Recording*, Circulation 77 (6): 1297–1305 (Jun. 1988).

AMP Piezo Film Sensors Product Guide Catalog 65711 Issued Apr. 1995.

*Primary Examiner*—Robert L. Nasser
*Attorney, Agent, or Firm*—Milde, Hoffberg & Macklin, LLP

[57] ABSTRACT

An apparatus for assessing cardiovascular status of a mammal comprising a system for locally applying a pressure to an artery, capable of restricting blood flow through said artery, a wideband external pulse transducer, having an output, situated to measure acoustic signals proximate to said artery, and a computing device receiving said output for calculating, based on said output, a peripheral vascular impedance value. The systolic and diastolic pressure are determined by an appearance and disappearance of a high frequency signal upon changes in cuff pressure partially occluding arterial blood flow. The arterial pressure waveform is estimated by measuring the wideband acoustic emissions from a non-occluded artery. The peak and trough of the arterial pressure waveform are calibrated with the determined systolic and diastolic pressures. The systemic vascular resistance is computed by occluding blood flow with a supersystolic pressure, and calculating, based on a natural logarithm of a difference in amplitude between a first major systolic peak and first major systolic trough and an amplitude of a second major systolic peak, a first order linear equation, which may be normalized for body surface area. The data obtained may also be used to analyze cardiac output, arterial compliance and dp/dt.

57 Claims, 6 Drawing Sheets

U.S. PATENT DOCUMENTS

| | | | |
|---|---|---|---|
| 5,297,556 | 3/1994 | Shankar | 128/668 |
| 5,298,602 | 3/1994 | Shikinami et al. | 528/361 |
| 5,301,679 | 4/1994 | Taylor | 128/773 |
| 5,307,818 | 5/1994 | Segalowitz | 128/696 |
| 5,309,917 | 5/1994 | Wang et al. | 128/696 |
| 5,331,968 | 7/1994 | Williams et al. | 128/721 |
| 5,337,752 | 8/1994 | Reeves | 128/700 |
| 5,339,290 | 8/1994 | Greenstein | 367/163 |
| 5,339,818 | 8/1994 | Baker et al. | 600/495 |
| 5,355,890 | 10/1994 | Aguirre et al. | 128/680 |
| 5,363,344 | 11/1994 | Sofen | 367/157 |
| 5,365,937 | 11/1994 | Reeves et al. | 128/715 |
| 5,370,122 | 12/1994 | Kunig et al. | 128/670 |
| 5,379,774 | 1/1995 | Nishimura et al. | 128/666 |
| 5,388,163 | 2/1995 | Elko et al. | 381/191 |
| 5,390,679 | 2/1995 | Martin | 128/673 |
| 5,391,190 | 2/1995 | Pederson et al. | 607/23 |
| 5,409,009 | 4/1995 | Olson | 128/661.08 |
| 5,446,826 | 8/1995 | Otsuki | 395/3 |
| 5,448,681 | 9/1995 | Khan | 395/11 |
| 5,480,412 | 1/1996 | Mouchawar et al. | 607/6 |
| 5,496,361 | 3/1996 | Moberg et al. | 607/122 |
| 5,497,778 | 3/1996 | Hon | 600/485 |
| 5,509,423 | 4/1996 | Bryars | 128/690 |
| 5,509,424 | 4/1996 | Al-Ali | 128/692 |
| 5,511,553 | 4/1996 | Segalowitz | 128/696 |
| 5,533,511 | 7/1996 | Kaspari et al. | 600/494 |

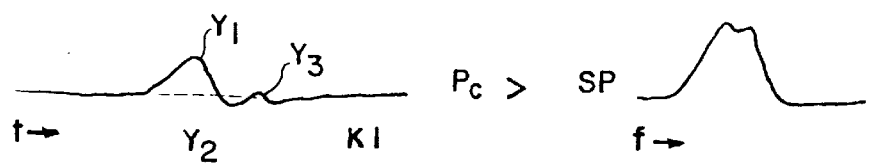
FIG.1
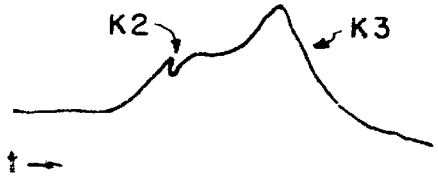
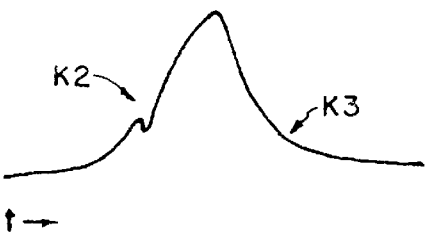
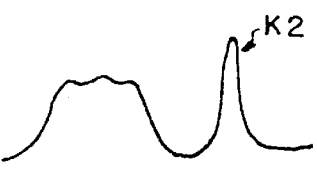
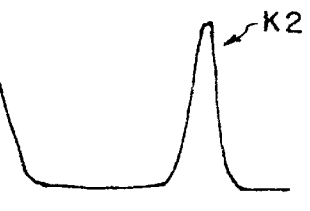
FIG.2
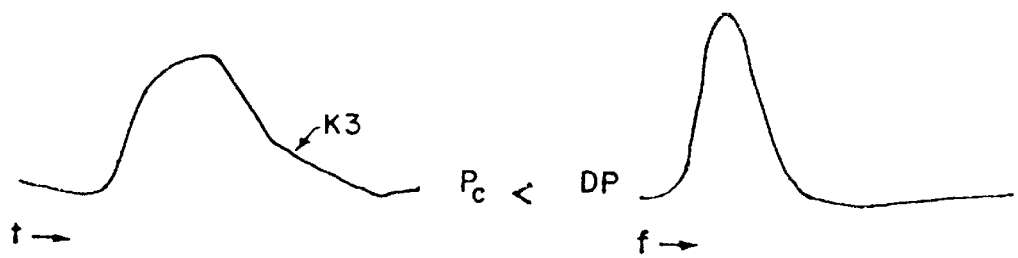
FIG.3

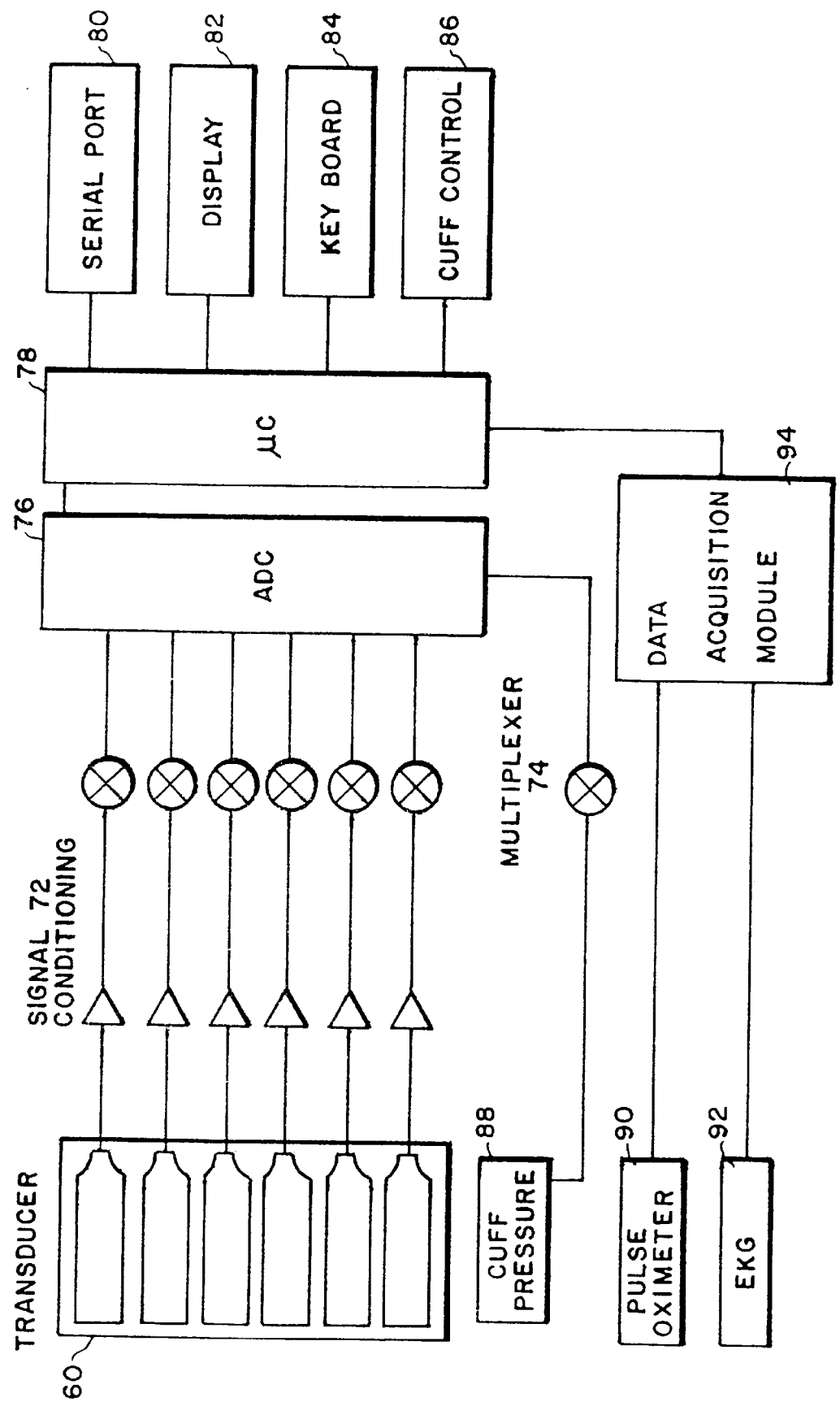

WIDEBAND EXTERNAL PULSE CARDIAC MONITOR

FIELD OF THE INVENTION

The present invention relates to the field of automated noninvasive peripheral vascular and cardiac output status monitoring based on analysis of vibrational signals with varying applied external pressure, and more particularly to noninvasive wideband external pulse (WEP) monitoring.

BACKGROUND OF THE INVENTION
CONVENTIONAL PRESSURE MONITORING

It is long known that peripheral blood pressure (BP) may be estimated using a sphygmomanometer and stethoscope. In this case, when the cuff pressure is between the systolic and diastolic pressures, a sound, called a Korotkoff sound, is heard. By determining the cuff pressure at which sounds are audible through a stethoscope, both systolic (SP) and diastolic (DP) pressures may be estimated. It has been found that the blood pressures so obtained correlate with various physiologic conditions and have both diagnostic and prognostic value. However, using standard techniques, errors in blood pressure determination may occur. These errors are especially common when defining diastolic pressure.

In a manual method of measuring a patient's blood pressure in non-invasive manner, a cuff is applied to an arm of the patient and pumped up to a pressure above the systolic blood pressure of the patient. The arteries of the patient are thereby pressed together in an occluding manner. The cuff pressure is then continuously decreased while the physician or the nurse monitors by means of a stethoscope the start and the end of the opening of the arteries in order to determine on the basis of these so-called Korotkoff sounds: the upper, systolic and the lower, diastolic blood pressure by simultaneously reading these values off from a manometer.

There are also automatic methods for performing this measurement, called "auscultation techniques". The blood pressure monitors employing this technique are not deemed reliable, and in fact are subject to errors and artifacts. In addition, often these techniques produce a result which fails to reveal useful clinical information. One such device is disclosed in U.S. Pat. No. 5,509,423.

Blood pressure monitors and blood pressure measuring methods, respectively, have been employed for a number of years in which the so-called oscillometric methods are utilized, which employ the oscillations or fluctuations of the walls of the arteries which occur in synchronism with the blood pulse. According to the oscillometric techniques, a cuff is pumped up to a pressure beyond the systolic pressure and is then deflated in discrete steps. Alternatively, a cuff is inflated in discrete pressure steps up to a predetermined measure beyond the systolic pressure. There is no universally accepted scheme for measuring blood pressure using oscillographic methods; however there are a number of commonalties in the various proprietary techniques.

During each step, where the cuff pressure is held substantially constant (to avoid artifacts), see, e.g., U.S. Pat. Nos. 4,349,034, and 4,074,711 and European Patent Nos. EP-A-208520, EP-A-353315, and EP-A-353316, or continuously inflated or deflated, see, e.g., U.S. Pat. No. 4,625,277 and European Patent Nos. EP-A-249243 and EP-A-379996, a pressure sensor detects the oscillations caused by movement of the arterial walls and superimposed on the cuff pressure. The amplitudes of these oscillations are recorded. It is thought by many that the oscillations, at the systolic or diastolic pressure, respectively, have an amplitude value or peak-to-peak value that is a fixed percentage of the maximum amplitude or maximum peak-to-peak value at mean pressure. Other criteria for translating oscillometric waveform data into blood pressure are known, and employed in the art. Thus, in the oscillometric measuring method the pressure determined as systolic or diastolic pressure generally is the pressure at which the amplitude or peak-to-peak value of the oscillations is at a specific cutoff, e.g., a percentage of the maximum amplitude of the oscillations.

These various oscillographic blood pressure measurements are prone to artifacts. Typical disturbances superimposed on the pressure signal are movements of the patient and muscular tremor such as shivering. In addition, there are physiological peculiarities, including arrhythmias, such as bigeminy and trigeminy, as well as the cyclic changes of BP due to respiratory variation. In the case of respiratory variations, these changes are real, and may themselves have diagnostic significance.

Oscillometric blood pressure monitors may selectively disregard oscillations, which are related to artifacts. An artifact in known blood pressure monitors is recognized on the basis of a criterion derived from the so-called oscillation channel. In oscillometric blood pressure monitors, the oscillation channel is understood to be a signal channel obtained on the basis of the so-called pressure channel signal, which constitutes the pressure sensor output, by high-pass filtering. This oscillation channel thus corresponds to the harmonic waves or oscillations superimposed on the pressure channel, disregarding the constant component. According to some known systems, this oscillation channel signal is rejected as having a superimposed artifact when either the ascending slope of an oscillation exceeds a maximum increase value or when, at a pressure step, the amplitude difference of two adjacent oscillations exceeds a maximum value or when an envelope criterion is not fulfilled according to which an examination is made as to whether two oscillation amplitudes have not become more than double or less than half between two adjacent steps or when the time interval between two oscillations varies by more than a specific percentage of the average time interval. Such a system, however, is not capable of making a distinction between movement artifact, cardiac arrhythmia or respiratory superimposition. U.S. Pat. No. 5,355,890, incorporated herein by reference, relates to a system for oscillographic blood pressure measurement, employing pulse extraction techniques.

Because of the susceptibiity of the algorithm used in the known oscillometric blood pressure monitor, both erroneous measurements and unnecessary alarms occur. This is of significance in particular since such blood pressure monitors are often employed in operating rooms where a multiplicity of other parameters of a patient must also be monitored, which may all cause alarms. Such medical apparatus must therefore keep the number of false alarms as low as possible, however without risking the recognition of a genuine physiological alarm.

U.S. Pat. No. 5,222,020 describes a blood pressure measuring apparatus which is coupled with an occlusive cuff in order to acquire dynamics on a pulsatile wall motion of human artery responding to the occlusive cuff as its pressure is lowered. The instantaneous cuff pressure (Pc) is first obtained with a pressure transducer; then its value is displayed on a CRT in real time as height variations of a mercury manometer along with the dynamic parameters describing the pulsatile wall motion. The dynamic parameters are basically its displacement velocity and acceleration of the motion generated by blood flow pulsating against the lowering Pc, which reflects the mechanical cardiac cycle of heart as reported by F. Takeda, et al., in Med. Bio. Eng.

Comput., Vol. 29, Supplement Part 1, 1991 which is hereby incorporated by reference. See, M. Borow et al., Am. Heart J., Vol. 103, 1982; U.S. Pat. Nos. 4,718,428, 4,796,184, and 4,793,360.

U.S. Pat. No. 5,178,154, incorporated herein by reference, relates to an impedance plethysmographic method utilizing peak aligned ensemble averaging. U.S. Pat. Nos. 5,379,774 and 5,297,556, incorporated herein by reference, relate to impedance plethysmographs which measure arterial elasticity by changes in arterial volume. U.S. Pat. No. 5,331,968 relates to an inductive plethysmographic transducer.

U.S. Pat. Nos. 5,409,009 and 5,391,190 relate to implanted impedance plethysmography devices for use in association with pacemakers. U.S. Pat. No. 5,188,106 relates to an implanted ultrasound transducer for measuring cardiac output and controlling a pacemaker. U.S. Pat. Nos. 5,496,361 and 5,480,412 relate to cardiac wall accelerometers for control of a pacemaker.

U.S. Pat. No. 5,370,122 relates to a cardiac monitoring device.

DEVICES THAT MEASURE PVR

There are a number of available devices that noninvasively measure Cardiac Output (CO). They use a variety of technologies. Each of these technologies determines peripheral vascular resistance as a function of a determined flow and pressure. Thermodilution is an invasive procedure that carries a risk of mortality and is expensive. See, U.S. Pat. No. 5,241,966, incorporated herein by reference. Transthoracic Impedance monitors are difficult to use and do not provide accurate information. On the other hand, they are noninvasive and carry no risk. U.S. Pat. No. 5,309,917 relates to a system for impedance plethysmography, a technique for noninvasive cardiac monitoring. Echocardiography is also noninvasive, but is expensive, relatively inaccurate and requires a skilled technician.

U.S. Pat. No. 5,390,679, incorporated herein by reference, relates to a cardiac output determining device which senses an arterial pressure waveform and compares the sensed waveform to a plurality of stored waveforms representative of known states.

U.S. Pat. No. 5,265,615, incorporated herein by reference, relates to a method for measuring systemic vascular resistance based on an analysis of pressure waveforms including a first dichrotic notch.

U.S. Pat. No. 5,211,177, incorporated herein by reference, relates to a non-invasive vascular impedance measurement system using a modified Windkessel model of the arterial system.

WIDEBAND EXTERNAL PULSE MONITORING

When using the standard auscultatory BP measurement technique, only a very small percentage (approximately 10%) of the energy recorded is within the audible range. Thus, the majority of the energy is dissipated as low frequency signals. These signals can be detected using appropriate wideband transducers. Surprisingly, when using such transducers, signals can be recorded when the BP cuff is inflated above SP.

Description of WEP signal

When a bolus of blood is ejected from the left ventricle, by a heart beat, a (pulse) wave of energy is created which travels from the heart to the periphery of the arterial system. When the energy wave comes up against a barrier (in this case where the arteries become very tiny arterioles), the wave is reflected back into the circulation, traveling from the periphery back towards the heart and great vessels. The majority of the energy in the pulse wave reflection is in the low frequency range. Both forward and backward waves can be recorded using a wideband low frequency transducer placed over the brachial artery.

Wideband external pulse (WEP) recording is based on the ability of a pressure sensor to record inaudible frequencies (down to 0.1 Hz) during blood pressure cuff deflation. Three distinct components of the WEP signal can be detected, called K1, K2 and K3.

The K1 Signal

With cuff pressure above SP (at a point when no Korotkoff sounds are audible), a low frequency signal (K1) is present. For each individual, K1 has a characteristic shape generally consisting of 2 systolic peaks and 2 troughs. The second trough represents the separation of the systolic and diastolic portions of K1. The early peak represents the energy generated by the contraction of the heart as the pulse wave travels from the heart toward the periphery. The early systolic K1 pattern is determined by ventricular ejection (stroke volume) and large artery stiffness.

The second (late) systolic K1 peak represents a measure of arterial pulse wave reflection. Wave reflection in the arterial system occurs from arterial terminations i.e. the arteriolar bed. Peripheral vascular resistance is a measure of the degree of contraction of the arteriolar bed. Since the level of vasoconstriction of the arteriolar bed is the major factor for both peripheral vascular resistance ("PVR") and the intensity of pulse wave reflection, the K1 pattern varies with measure peripheral vascular resistance. Other factors, such as age (i.e. arterial stiffness) may be involved in the baseline K1 pattern, but acute changes are due to changes in PVR.

K1 Analysis—Description of K1R

Three vectors are defined from baseline: the initial peak (Y1), the subsequent trough (Y2), and the second systolic peak (Y3), as shown in FIGS. 9A and 9B. FIG. 9A shows a typical K1 pattern of a young person with normal blood pressure, while FIG. 9B shows a typical K1 pattern of an elderly hypertensive patient.

These patterns (K1 pattern) are reproducible in individuals, tend to change with age, yet have been found to vary in different physiological states. Analysis of these waves has led to a derivative called the K1Ratio and the related K1R.

A K1 Ratio is calculated by:

$$K1\ \text{Ratio} = (Y1 - Y2)/Y3$$

$$K1\ R = \ln(K1\ \text{Ratio})$$

Thus, K1 R is the natural log of the K1 Ratio.

It has been demonstrated that this ratio declines with age, but more importantly, can change many-fold in a particular individual depending upon the state of vasodilatation. Thus, the concept has been developed that changes in K1R (and the K1 Ratio) are due to changes in reflectance of waves in the circulation. As such, K1R can be used as a direct measure of both the physical properties of large arteries and the degree of peripheral vasomotor tone.

The K2 Signal

K2 appears at SP and disappears at diastolic pressure, which approximately corresponds to the audible Korotkoff sound. The appearance/disappearance property of K2 is the basis for an objective and more accurate method for measuring blood pressure, called K2 analysis. A legitimate Korotkoff sound cannot be present without the visual presence of K2.

K2 Analysis

The K2 analysis technique using Wideband External Pulse (WEP) recording correlates better with the intraarterial blood pressure than the auscultatory technique. Blank, S. et al., Circulation, 77:1297–1305,1988. See also, Blank, Seymour G., "The Korotkoff Signal and its Relationship to the Arterial Pressure Pulse", Ph.D. Thesis, Cornell University (1987) (UMI 8810638), expressly incorporated herein by reference.

The presentation of WEP data in more than one dimension has been the subject of some study. Denby, L. et al., "Analysis of the Wideband External Pulse: An application of Graphical Methods", Statistics in Medicine, 13:275–291, 1994.

There are situations in which the auscultatory technique has acknowledged difficulty. These include the presence of auscultatory gaps, pregnancy, and narrow pulse pressures.

WEP measurements have been proposed to assist in the interpretation of peripheral blood pressure measurements in the presence of auscultatory gaps. Blank, S. et al., "Characterization of Auscultatory Gaps With Wideband External Pulse Recording", Hypertension, 17(2):225–233, 1991.

In pregnancy and narrow pulse pressures, WEP measurements have been used as a validation standard with which to evaluate the auscultatory technique. Blank, S. et al., "How should diastolic blood pressure be defined during pregnancy?", Hypertension, 24:234–240,1994. Blank, S. et al., "Isolated elevation of diastolic blood pressure: real or artifactual?" Hypertension, 26:383–389, 1995. WEP has also been employed to assess underdeveloped K2 (auscultatory gaps) with respect to vascular stiffness and atherosclerosis. See, Cavallini et al., "Association of the Auscultatory gap with Vascular Disease in Hypertensive Patients", *Ann. Intern. Med.* 124:877–883 (1996).

The K3 Signal

K3 appears with cuff pressure between SP and DP and continues to be present below DP. K3 resembles the intraarterial pressure waveform. Thus, when calibrated according to K2 analysis (i.e. SP and DP), direct determinations of mean arterial pressure and noninvasive dp/dt measurements can be made.

Measurement of Mean Arterial Pressure from WEP Recording

The determination of mean arterial pressure is traditionally based on the formula:

MAP=Diastolic Pressure (DP)+$k$x(SP−DP)

where k represents a form factor which is generally assumed to be $\frac{1}{3}$. In actuality, k depends on the shape of the intraarterial pressure pulse, and can vary from 0.2 to 0.5. Thus, significant errors can occur when calculating MAP in the traditional manner (from SP, DP and k factor).

Using WEP Recording, DP and SP can be accurately determined using K2 Analysis. Since K3 closely resembles the intraarterial pulse, and can be calibrated according to analysis of K2, MAP can be directly measured from the area under the curve. Analysis of K3 can yield an accurate measure of the k factor mentioned above.

Physiological Studies Relating K1 Ratio to Peripheral Vascular Resistance

In 12 elderly patients, immediately prior to undergoing major joint replacement surgery, measurements of K1Ratio (and K1 R), cardiac output (CO), peripheral vascular resistance (PVR) and other hemodynamic variables were concurrently measured during 5 different physiological states. These included infusions of epinephrine (E) and norepinephrine (NE) both before and following epidural blockade. The results of this study were published in 1994 ("Comparison of Changes in K1 ratio and Systemic Vascular Resistance following Epidural Anesthesia as indices of Vasodilatation", ASRA Annual Meeting 1994, p. 69).

Assessment of Cardiac Contractility Using WEP Recording

A measure of cardiac contractility can be determined noninvasively by determining the rate of rise of a calibrated K3 signal using the so-called dp/dt concept. Similarly, a measure of cardiac contractility may be derived from the upstroke of a calibrated K1 pattern.

Systems for Measurement of Wideband External Pulse

According to the prior art, the system designed to measure wideband external pulse (WEP) acoustic emissions employs high precision, large dynamic range foil electret microphone with a linear high impedance electrometer.

Various piezoelectric materials are known, which are able to convert vibrations or movements into electrical impulses. These may include polyvinylidene fluoride polymers, e.g., Kynar®, or polylactic acid. See, U.S. Pat. No. 5,298,602. AT&T provides a type of wideband Foil Electret Sensor, with no significant change in sensitivity under a pressure range of at least 0 to 250 mm Hg, with sensitivity over its entire surface and a flat (−3 dB) bandwidth of from below 0.1 Hz to above 2000 Hz. Therefore, such a Foil Electret microphone may be used as a wideband acoustic transducer in an apparatus to obtain the wideband external pulse, connected to a high impedance ($10^9\Omega$) amplifier, such as a Keithly electrometer (Model 600B) (Keithly Instruments, Cleveland Ohio) and then to a direct current amplifier model DCV-20 of an Electronic for Medicine/Honeywell model VR6 physiologic recording system (Electronics for Medicine, Pleasantville, N.Y.).

The known device includes an inflatable cuff for encircling the arm and receiving vibrational signals over the brachial artery. The cuff pressure may be controlled by a Hokanson E-10 cuff inflator (Hokanson, Issaquah Wash.) and the pressure may be manually read with a mercury column or a Gould-Stratham P23 ID or T4812 AD-R (Gould-Stratham, Oxnard, Calif.) pressure transducer connected to the physiologic recording system through a PDV-20 amplifier. The deflation rate of the Hokanson unit is manually set to about 2–4 mm Hg./sec.

The wideband acoustic data may be analyzed with a computer system, such as a DEC LSI 11/23 computer, sampling at 400 samples per second with 12 bit resolution. An IBM PC/AT or equivalent may also be used, sampling a 12 bit analog to digital converter at 500 samples per second, using CODAS (Dataq, Akron Ohio) data acquisition software.

Other Transducer Systems

An electret transducer array, as disclosed in U.S. Pat. No. 5,388,163, incorporated herein by reference, may be constructed of an electret foil and a backplate. The electret foil is flexible, having two layers, a metal (such as aluminum) layer and a synthetic polymer (such as PTFE Teflon®) layer. The metal layer may be, e.g., two thousand Angstroms thick, while the polymer layer may be, e.g., between 2–100 microns thick. The polymer layer is given a permanent charge, to form an electret, to a predetermined value at, e.g., −300 volts, by conventional techniques. A positive compensating charge is induced in the backplate and the metal foil layer.

The electret element is situated to be sensitive to the acoustic waves traveling in the tissue. Thus, a mounting is provided which provides a vibration-free reference. Thus, any piezoelectric activity in the electret element is presumed due to relevant acoustic waves and not artifact. Thus, the transducer is used to detect vibrations from the brachial artery through skin and tissue. A backplate may be formed of a sintered or porous material to allow air flow behind the element while providing structural rigidity.

Multiple segments of an electret transducer array may be formed by the selective removal of the metal layer from the electret foil to achieve transducers of any desired shape, size, and location. Selective removal of portions of the metal foil layer for the purpose of forming segments may be accomplished by etching or dissolving the metal using a chemical reagent, such as a solution sodium hydroxide or ferric chloride, or otherwise in known manner with a variety of chemical and/or photoetching treatments.

Alternatively, segments may be defined on the foil prior to charging and mounting on the backplate. This may be done by selectively metalizing the polymer layer to form a foil. Selective metalization may be performed by conventional metal deposition techniques (e.g., masking, evaporation, sputtering, etc.) to form segments of any desired size, shape, and location. A continuous electrode foil having a polymer layer selectively charged (with either or both polarities) in defined locations may also be used.

Electrical leads are coupled to each individual electrode segment. Also provided is an electrical lead, coupled to the backplate, which may serve as a common lead for the transducers of the array. The electrical leads for the segments may also be formed as conductive traces on the surface of the electret element, preferably electrically insulated from the surface. By means of these leads, electrical signals produced by each transducer in response to incident acoustic signals may be accessed for amplification and other processing.

An alternative piezoelectric transducer may be used as a hydrophone, as disclosed in U.S. Pat. No. 5,339,290. Typical suitable polymers include PVDF, but the copolymer P(VDF-TrFE) is preferred because of its flexibility with regard to the poling process that is conventionally employed in defining a piezoelectrically strong active area. For example, the active area may be provided at the center of the piezoelectric membrane, which may be a single-sheet type or bilaminate. U.S. Pat. No. 5,365,937 relates to a piezoelectric transducer for receiving heart sounds. U.S. Pat. Nos. 5,337,752 and 5,301,679 relate to systems for the analysis of body sounds.

As disclosed in U.S. Pat. No. 5,363,344, a transducer may be formed of a material called C-TAPE by C-TAPE Developments, Ltd., 3050 S. W. 14th Place, Boynton Beach, Fla. 33435. This material is the subject of U.S. Pat. No. 4,389,580, hereby incorporated by reference.

Therefore, the prior art discloses systems capable of obtaining wideband external pulse ("WEP") signals under laboratory conditions, and further discloses studies analyzing data so obtained to determine blood pressure. The prior art acknowledges the richness of the information included in the WEP signals, but does not teach or suggest how this information may be extracted and employed to determine the cardiac status of an individual patient, other than blood pressure, and further does not disclose automated instruments for obtaining and analyzing the WEP data. Therefore, the prior research of the present inventor remains inaccessible in a clinical setting.

SUMMARY OF THE INVENTION

The present inventor has therefore sought to implement systems and methods to obtain reliable WEP data from patients in a clinical, office or home setting, and to analyze this data to produce not only reliable blood pressure ("BP") readings, but also cardiac output ("CO") and peripheral vascular resistance ("PVR") determinations.

The WEP data may also be analyzed to produce composite indicators of diagnostic or prognostic implication, which need not be directly related to traditional cardiovascular status determinations. Further, because the WEP data is multidimensional, it may be presented in a variety of ways to easily convey the complex information.

In analyzing the WEP data, the K1, K2 and K3 data from the WEP transducer are analyzed to yield significant information. However, an instrument may also include additional transducers for detecting other physiological parameters, which may be analyzed and presented separately or employed to provide improved indication of cardiovascular status.

CARDIOVASCULAR STATUS CALCULATIONS

Most of the energy generated under a blood pressure (BP) cuff contains frequencies below the audible range. In conjunction with a sphygmomanometer, a pressure sensor system having sensitivity down to 0.1 Hz, i.e., −3 dB sensitivity, produces a reproducible graphic pattern called the wideband external pulse (WEP). Three particular components of the WEP have been identified having particular significance, called K1, K2 and K3. The K1 signal is recorded with cuff pressure above systolic pressure, i.e., where no Korotkoff sounds are heard. The K1 signal generally exhibits three peaks of varying amplitude separated by two troughs. The second trough separates the systolic and diastolic portions of the cardiac cycle. The shape of the K1 is believed to be related to the physical properties of the arterial system. K2 appears and disappears at systolic pressure (SP) and diastolic pressure (DP) respectively. The appearance/disappearance property of the K2 may be used to accurately measure BP. The K3 resembles an intraarterial (peripheral) waveform, which can be calibrated with the K2 analysis to allow accurate mean arterial pressure and dp/dt determination.

According to the present invention, the waveform derived from the wideband external pulse sensor may be analyzed and changes in cardiac output and stroke volume for a given patient may be derived. Thus, a non-invasive monitor may be provided to determine cardiac and circulatory status of a patient. It has been found that by assessing the K1 ratio, PVR and changes in PVR can be assessed (see infra). By concurrently determining blood pressure by analysis of K2 and analyzing the K3 waveform, the mean arterial pressure (MAP) may be accurately determined, and CO may be derived according to the formula CO=MAP/PVR, or to obtain results in liters per minute, CO=80(MAP)/PVR in commonly expressed units. The various cardiovascular factors may be updated frequently, e.g., every 1–2 minutes. Since the K1, K2 and K3 waveforms are measurable from an external cuff, the need for invasive procedures or multiple instruments is eliminated. It is noted that full, unabridged cuff inflation/deflation cycles may not be necessary under certain circumstances, so that rapid measurements of CO may be obtained, from truncated measurement cycles.

The heart rate ("HR") can also be easily determined by WEP recording. Consequently, stroke volume ("SV") of a heartbeat can be calculated by the CO divided by HR:

$$SV = CO/HR$$

The inventors hereof have found that, for a given individual, the shape of the K1 pattern, as expressed by the K1 ratio, is related to biometric factors and PVR, over a wide range of arterial pressures with varying hemodynamic conditions, i.e., changes in CO and vasomotor tone. Thus, for each patient, the in (K1 ratio) is very closely correlated with PVR over the entire range of conditions. Since MAP (K2 and K3 analysis) and PVR (K1 analysis) are independently assessable, CO may be computed each time a measurement is made, e.g., a full cycle of cuff inflation/deflation.

Thus, for an individual patient, relative changes in cardiovascular status may be monitored by non-invasive means, and once calibrated, absolute indications of cardiovascular status may be assessed.

There is no established "gold standard" for the measurement of arterial stiffness. Population cross sectional data demonstrates that the K1 ratio and K1R are seen as strongly correlated to different measures of arterial stiffness. In regression analysis, when age is included in the analysis, arterial stiffness drops out as an independent factor, suggesting that the resting K1 pattern may reflect arterial structural changes associated with the aging process. The monitor according to the present invention, by directly measuring arterial compliance, can therefore be used to assess degenerative diseases of large arteries (including the aging process).

The Peripheral vascular resistance is a known metric which, when multiplied by cardiac output, yields the mean arterial pressure. On the other hand, there are broader concepts which relate to the relationship of blood pressure and flow, which also depend on the size and status of the mammal being evaluated Thus, by analyzing biometric factors in addition to WEP data, the standard metrics may be calculated. On the other hand, it may also be valuable to evaluate the standard metrics such as PVR, CO and MAP in view of biometric differences. For example, a mammal with a larger body mass would be expected to have a larger cardiac output and therefore lower peripheral vascular resistance. Therefore, in order to include such biometric considerations, the concepts are referred to herein as peripheral vascular impedance value ("PVI"), indicating this more complex relationship. One specific PVI representation, known in the study of cardiovascular status, is the PVRI, or the peripheral vascular resistance indexed for body surface area.

The size of the vascular tree of a given mammal tends to be correlated to its body surface area; therefore, the larger the surface area, the greater the amount of peripheral tissue, and the greater the vascular tree supplying that tissue. It is hypothesized by the present inventors that the effects of the peripheral vasculature on the K1 signal varies dependent on the size of the vascular tree. Thus, it is believed by the present inventors that the PVR calculation may be normalized for this effect by reference to body surface area.

There is thus believed to be a physiological basis for a relationship between K1R (ln[K1 ratio]), and PVRI. When a pressure pulse is generated by the heart, it creates a (pulse) wave of energy which travels from the heart to the periphery of the arterial system. When the energy wave comes up against a barrier (in this case where the arteries become very tiny arterioles), the wave is reflected back into the circulation, traveling from the periphery back towards the heart and great vessels. The majority of the energy in the pulse wave reflection is in the low frequency range. This energy signal can be recorded using a wideband low frequency transducer placed over the brachial artery as WEP data, providing there is no blood flowing through it. The brachial artery is occluded by a pressure cuff (inflated above systolic pressure). Thus, this is a biological signal whose physiological significance has been hitherto unrecognized.

The present invention therefore includes the detection of these low frequency signals for:

analysis of a derivative of the K1 waveform—K1R;

measurement of PVRI (and PVR) from its relationship to K1R;

measurement of MAP from K2 and K3 analysis;

calculation of cardiac output from MAP and PVR;

derivation of a measure of arterial compliance by knowing PVR and the slope of the decay from K3; and measurement of cardiac contractility from the upslope of K1 or K3.

Therefore, according to the present invention, significant cardiac status may be calculated by relatively simple analysis of the WEP data. The present invention therefore provides a system and method for obtaining and analyzing the WEP data to determine cardiovascular status.

As stated above, in 12 elderly patients undergoing major joint replacement surgery, measurements of K1 Ratio (K1R), CO, PVR and other hemodynamic variables were concurrently measured during 5 different physiological states, including infusions of epinephrine (E) and norepinephrine (NE) both before and following epidural blockade. See, "Comparison of Changes in K1 ratio and Systemic Vascular Resistance following Epidural Anesthesia as indices of Vasodilatation", ASRA Annual Meeting 1994, p. 69. Reanalysis of this data by the present inventors, relating the K1R (ln [K1Ratio]) to peripheral vascular resistance index (PVRI) demonstrated a tight relationship (r=0.96).

The determined relationship between K1R and PVRI, which is PVR indexed to body surface area, is:

$$K1R = -0.004 \times (PVRI) + 3.217$$

or $$PVRI = (3.217 - K1R) \times 250$$

From these equations, when K1R=0, PVRI=714 dyne sec $cm^{-5}m^{-2}$. Furthermore, for every change of K1R of 1, PVRI changes by 250 units. Thus, with the above formula and correction for body surface area, K1 analysis can be used to directly and noninvasively measure PVR. As stated above, once PVR is determined, CO can be derived using measurements of MAP using the formula CO=MAP/PVR, or CO (L/min.)=80(MAP)/PVR.

These specific mathematical relationships between K1R and PVRI were derived from a relatively homogeneous patient population of elderly patients undergoing total joint arthroplasty. The relationship is first order linear, and has a high correlation coefficient (r=0.96), verifying the physiological significance of the relationship. Nevertheless it is possible that the exact mathematical relationship between K1R and PVRI may vary in certain populations, e.g., obstetric patients or neonates. Further, it may be found that, under certain circumstances, a different biometric compensation is necessary to determine PVR. Therefore, for each subpopulation, the of K1R and PVI may be determined, with the algorithm selected based on the patient subpopulation identification as necessary. It is also noted that in particular instances, the K1 signal may be analyzed in a more sophisticated manner, to determine characteristics of the arterial system.

Arterial Compliance can be derived using a first order Windkessel model of the circulation by measuring the downslope of the K3 signal. The time constant of the exponential downslope equals (PVR)×(Arterial Compliance). Since we can determine the downslope directly from K3, and the PVR from K1R, we can compute Arterial Compliance:

$$C = \tau_{K3}/PVR$$

Arterial compliance measured noninvasively by WEP recording may provide hitherto unobtainable information on degenerative diseases of large vessels such as atherosclerosis, calcification of great vessels, and hardening of the arteries from aging and hypertension.

Likewise, cardiac contractility may be determined by analyzing the K1 or K3 upslope.

Furthermore, because of the richness of the data obtained by WEP analysis, the presentation need not be limited to known parameters, and in fact the WEP system according to the present invention may be used to generate composite indices with prognostic or diagnostic significance. Further, while the inventors hereof have found that standard cardiovascular indices may be determined by relatively simple analyses, more complex analyses of the WEP data may be conducted, using algorithms, neural networks or the like to produce known or new relationships between the WEP data and prognostic or diagnostic measures. Further, while the simple calculations generally required to obtain cardiovascular status are often sufficient, exceptions, if any, to these calculation forms may be identified and corrected to improve reliability. Neural networks are known processing systems for determining the solution to problems which are very difficult to handle by means of conventional logic systems, or where the logic or algorithm is complex or not well understood. Neural networks are generally programmed by "training" with data sets, rather than by explicit definition of their expected behavior. While conventional methods require complex algorithms, which explicitly formulate the relationship between input variables, neural nets "learn" the relationship between the variables. For each neural net, the connections and/or weighting of connections must be provided so that for a given input pattern the neural net generates an appropriate output pattern. See, D. E. Rumelhart et al., "Learning Internal Representations by Error Propagation", in D. E. Rumelhart & J. L. McClelland (Eds.), Parallel Distributed Processing: Explorations in the Microstructure of Cognition (Vol. 1), pp. 318–362, MIT Press, 1986, Cambridge, Mass. See also, U.S. Pat. No. 5,253,329, incorporated herein by reference. Neural Network methods may be combined with fuzzy logic techniques in order to provide expert input into the processor operation. See U.S. Pat. Nos. 5,448,681 and 5,446,826, incorporated herein by reference.

Therefore, given the richness of the cardiovascular status information contained within the WEP signal, a neural network may be trained to associate WEP signal patterns and prognostic or diagnostic information. For example, a large series of persons may be subjected to WEP surveillance along with traditional medical care. Data is retained including raw or processed WEP signals, as well as details of other clinically significant parameters, diagnoses and outcomes. After a large amount of data is obtained, it is used to design and train a neural network to relate the WEP signal data with the diagnoses and outcomes which were determined for each patient. Other clinical data may also be included in the analysis, design and training. The trained neural network may then be able to receive WEP signal data and possibly other information and output information predicting diagnosis or outcome. Where this prediction has a low error, e.g., root mean square error over the training data set or an identifiable subpopulation thereof, the neural network may then be employed as a diagnostic or prognostic tool.

TRANSDUCER

A variety of transducer types may be used in the present invention. For example, one version may use a more expensive transducer which would be non disposable. Alternately, cheaper transducers for simpler monitors may be used. Finally, a version may include a disposable cuff for use in patient care environments where infection control is an issue e.g. intensive care, emergency room, neonatal units. The disposable version may also include a separate sensor which is secured over the brachial artery with an adhesive. Once placed, this would also facilitate comparison of repeated estimations with changing physiological states and make it easier for nursing staff to oversee.

The preferred wideband acoustic transducer according to the present invention has an acoustic sensitivity over the range 0.5–500 Hz, and more preferably at least 0.1–5000 Hz, under application of a range of 0–300 mm Hg applied pressure. Further, the effect of pressure is preferably predictable and repeatable under a range of environmental and applied conditions. Therefore, it is apparent that the lower range of sensitivity extends well below the normal audible range, and further that normally compensated audio componentry is generally insufficient, having a −3 dB lower cutoff of around 20 Hz. Normal pressure transducers, on the other hand, have the low frequency sensitivity, but may fall short on the upper end, and are not generally sensitive enough or configured properly to accurately receive the WEP acoustic signal. It has been found that electret transducers, known in the art, are suitable as wideband acoustic transducers under the pressure cuff. However, prior transducers were laboratory instruments, having high cost and limited availability. Further, when the transducer is integrated into a system, external compensation may be applied to allow use of transducers which have low selectivity, being sensitive to a number of environmental factors, in addition to acoustic vibrations.

A low cost system may therefore be implemented using a metalized Kynar® sheet transducer (ELF Atochem/AMP Sensors). Kynar® is a polyvinylidene fluoride (PVDF) homopolymer or copolymer, formed as a sheet. This sheet has a high dielectric strength of about 30 V/mil, and is highly piezoelectric. A metalized 22 mil Kynar® sheet has a source impedance of about $10^{13}$ Ω per square, thus requiring a relatively high impedance amplifier for linear wideband operation. Alternatively, the electret transducer may be integrated with a charge balancing amplifier, providing a direct pulse modulated output from the transducer system.

Another alternative transducer system that may be used is the "acoustic contact sensor" ARC model 701010, available from Apollo Research Corporation, Depew N.Y. This device can easily be modified to achieve the required low frequency response (0.1 Hz) of, e.g., the "pulse pressure transducer" ARC model 701012, while having a housing suitable for situation under a pressure cuff.

It is preferred to localize the sensitive area of the transducer over the brachial artery at the distal edge of the cuff, to maintain a high signal to noise ratio and reduce artifacts. Therefore, one aspect of the invention involves simplifying the placement of the WEP transducer over the brachial artery. This may be done in a number of ways. First, the WEP signal may be obtained during manual placement, seeking the maximum signal amplitude, presumably when the transducer is over the artery. Alternately, a multisegmented transducer is provided which is placed generally over the artery, so that the segment or segments which have the maximum signal amplitude or otherwise determined to have optimal placement may be used in subsequent analysis. By segmenting the wideband external pulse transducer, a number of advantages may accrue. First, by localizing an active segment or segments over the artery of interest, generally the brachial artery, the signal to noise ratio of the signal will be increased. Further, various artifacts may be minimized in relation to the signal of interest. Transducer segments located distal from the artery of interest may be used as control segments, allowing compensation of characteristics of the active segment. A segmented electrode system may also allow phase differentiation of tissue or vessel acoustic conduction, and allow implementation of a phased array transducer. The output of the phased array may be processed in known manner to detect the location and nature of a signal source, and to differentiate various signal sources, allowing effective filtering.

In one embodiment, the metal foil layer of the electret foil is provided as a plurality of discontinuous segments. These segments define the shape, size, and location of the active areas of individual electret transducer elements in the array. Data from a number of such segments may be obtained. This allows, for example, segmentation of the transducer into regions, one or more of which may be used to measure the arterial pulse, and optionally allowing one or more regions as compensation segments to identify and compensate for artifacts, environmental factors and interference.

Like the individual segments defining transducer shapes, the array itself may be formed of any size and shape. So, for example, the present invention may provide a single planar transducer, or a multiple transducer array curved to fit a three-dimensional contour. The known foil electret transducer includes a stiff support member. A film transducer according to the present invention also preferably includes a stiff support, or may be provided as a flexible member under the pressure cuff in such configuration to retain low frequency sensitivity and relative isolation from changes in output due to changes in cuff pressure.

By employing a low cost polymer film transducer with appropriate electronics for conditioning and compensating the high impedance signal, a mass produced device is possible. In addition, by employing a metalized polymer film transducer, the transducer may be well integrated into the device, i.e., the cuff structure. This may therefore be used as an alternative to the higher cost electret transducer.

Unlike well compensated sensors, raw PVDF films are both piezoelectric and pyroelectric, requiring temperature compensation for accurate long term output. However, if the temperature induced changes occur on a timescale much larger than acoustic emissions, then these may be separated by time filtering, or time filtering in conjunction with a temperature compensation circuit. It is noted that, in the present system, two effects may induce thermoelectric effects. First, the pulsatile arterial blood flow may produce cyclic temperature variations. Since the cuff intermittently occludes blood flow, the cuff inflation may induce thermal variations in the output of the transducer. However, these signals will generally be small, and even if significant, may be generally filtered from the true acousto-electric signal, e.g., by a model based filter implemented in the processing computer.

Electret materials, such as Kynar® (PVDF), may also be responsive to acceleration, vibration, flexion, and other environmental influences. In order to eliminate these unwanted influences from the desired measured variable, the system may compensate through measured or estimated effects of the confounding influences, and/or filtering of the signal to selectively transmit the desired portion of the output of the transducer. For example, a temperature sensor may be provided for temperature compensation of the entire transducer or portions thereof Likewise, artifacts due to movement, muscle contractions, or "crinkling" of the transducer during cuff pressure changes may be compensated by a transducer which is not subject to, or less subject to, the acoustic excitation, such as a transducer segment which is distal from the brachial artery but otherwise subject to a similar environment. A simultaneous ECG and/or respiratory status input may be used to provide synchronization for a time-based analysis, or synchronization may be based on arterial pressure pulses.

The PVDF sheet transducer may be provided with a segmented electrode pattern by etching an aluminum metalization with ferric chloride solution. A segmented electrode may be advantageously used to increase the signal to noise ratio by localizing the active portion of the acoustic sensor over the source of acoustic emissions, and optionally by providing compensation segments.

ELECTRONICS

High impedance electrometer amplifiers, e.g., low femptoamp range input currents, may be formed with JFET input stages, with input protection to prevent overload. These amplifiers may produce noise, especially at low frequencies. For example, the Analog Devices (Norwood, Mass.) AD549 amplifier has an input current of around 60 fA. Preferably, a single operational amplifier is provided per segment of the transducer. The outputs of the amplifiers may then be multiplexed and digitized and analyzed by a microcomputer system. Alternatively, in order to reduce costs in a multiple segment transducer, discrete JFETs may be provided to buffer the input from each segment of the transducer. The JFET circuit outputs may then be multiplexed, digitized and input to a microcomputer system for analysis. CMOS electrometer amplifiers are also available, such as the National Semiconductor LMC6001 amplifier.

Suitable analog to digital converters are available from a number or sources. For high resolution, which may simplify interface circuitry, Analog Devices AD1382, AD1385, AD676, AD677, AD776, AD1876, AD7701, AD7703, AD7872/7872, AD7882, AD7884/7885, AD7715 or AD7716, National Semiconductor ADC16071 or ADC16471 devices may be used. For systems with lower resolution, 12 bit integrated data acquisition system devices, e.g., National Semiconductor ADC12L03X, ADC213X, LM1243X, LM1245X, or Analog Device AD7858, AD7874 may be used.

Microprocessors having integral 10-bit (or greater) resolution analog to digital converters may also be used, including the Microchip PIC 16C74 (8 bit ADC), Siemens 80C167, Philips 89CE558 microcontroller (10 bit ADC), Hitachi H8S2653 (10 bit ADC). Of course, other microcontrollers with internal or external, preferably 10-bit or greater resolution ADC's may also be used. Where resolution is inadequate, a subranging design employing a digital-to-analog converter in the system is used to effectively extend resolution and compensate for drift and low frequency changes. A DC accurate switched capacitor high pass filter with a cutoff frequency below the lower frequency limit of the transducer, e.g., less than 0.1 Hz, may also be used to compensate for offset and low frequency effects to maintain the signal within an optimal range.

DSP systems, such as the Texas Instruments TLC320AC02 or TLC320AD58C and TMS320C3X, TMS320C5X or other digital signal processor and compatible analog interface devices may also be employed to process the WEP signal, especially where complex algorithms are executed. However, such devices are not considered generally necessary to perform simple K1, K2 and K3 analyses, but may be advantageous for complex neural network calculations.

While the WEP signal may be analyzed using a 8–10 bit analog to digital converter ("ADC") and an 8 bit microcomputer, the availability of cost-effective powerful system components makes their use preferable. The computer is therefore preferably an 8–32 bit microcomputer, interfaced with a 8–18 bit delta-sigma analog to digital converter having a sampling rate of in excess of about 4800 Hz, and a low frequency cutoff of below 0.2 Hz. The microcomputer may include DSP elements or be interfaced with a DSP for signal analysis, e.g., Texas Instruments 320CXX, Motorola 560XX, or Analog Devices ADSP-21XX.

On the other hand, as an outpatient monitoring device, the preferred system includes a highly integrated 8 or 16 bit microcomputer having an integral 8–10 bit ADC, with inputs receiving conditioned signals from the cuff pressure transducer and WEP transducer, as well as status inputs from the deflation valve and inflation pump motor. Keypad input and LCD output may also be provided. In addition, an audio interface, such as a piezoelectric element may be used as an enunciator or data output interface, and may also be used as an input device for limited voice commands or in the manner of an acoustic remote control. An infrared or telephone modem device may also be included.

CUFF MECHANISM

The blood pressure measurement apparatus for automatic non-invasive monitoring of a patient's blood pressure comprises a pressure cuff applied to an arm of the patient, a pump for inflating cuff, e.g., to a predetermined pressure, a pressure sensor for producing a pressure signal indicative of the pressure within the cuff, a valve system, e.g., driven by a microprocessor, for stepwise or continuous control of the pressure applied to a limb by the cuff and preferably for ensuring that between sequential heartbeats, the cuff pressure differs by a small amount.

Such mechanisms are standard and well known. The WEP of the present system is provided under the distal edge of the cuff and adjacent to an artery, generally the brachial artery.

A disposable cuff, for infection control or in situations where return of the cuff may be delayed or unlikely, may be formed of a plastic or rubber film or a reinforced film. For example, a polyurethane film bladder with fabric lamination may be employed. The transducer may be affixed to the cuff, or separately located on the brachial artery by adhesive. The cuff may be provided with a single or multiple tube connection to the pump, relief valve and pressure transducer, which are preferably reusable.

SIGNAL PROCESSING AND ANALYSIS

In order to analyze the transducer output signal(s), characteristics of the signal in both the time and frequency transform domains are relevant. These analyses may be conducted in a number of ways. For example, a frequency domain transform, e.g., DCT or Fourier transform may be employed, which may advantageously be used in conjunction with a filtering algorithm to filter various artifacts, such as muscle tremor and contraction induced output, which will show significant power in the range of about 6–10 Hz. Other types of artifacts and baseline drift due to cuff pressure deflation may also be filtered in this manner, or optimal filters applied based on predetermined models of the expected or known artifacts. This same frequency-domain transformed signal may also be used for processing the signal, e.g., K2 analysis, to determine events of relevance in the analysis proper. After filtering, an inverse Fourier transform may be employed to reconstruct the filtered time domain signal for aspects of the analysis, as necessary.

The filter may be adaptive, using e.g., fuzzy rules to identify and filter artifacts in the transducer output, based on their relative timing in the pulse waveform, vibrational characteristics and statistical parameters. By employing fuzzy logic paradigms, an expert defines preprogrammed rules which characterize set inclusion for multiple criteria, while allowing versatility and the ability to handle real data.

In order to perform analysis of the pulse pressure waveforms, it is necessary that a series of pulse pressure waveforms be acquired by the wideband external pulse transducer over a range of cuff pressures. Through signal analysis or external gating, such as by myocardial electrical synchronization (EKG), the beginning of each pulse pressure waveform is determined, and the pulse analyzed. Above systolic pressure, each pulse is analyzed for K1 analysis, useful for analysis of arterial system properties, e.g., PVR. At cuff pressures between systolic and diastolic pressures, K2 analysis is used to accurately determine intraarterial pressures. At cuff pressures below diastolic pressures, K3 analysis is used to determine mean arterial pressure, dp/dt and arterial compliance. The Cardiac output and stroke volume may then be determined. A computer receives data from the wideband external pulse transducer through an amplifier, signal conditioning electronics as necessary, and an analog-to-digital converter. Other physiological parameters may also be multiplexed and input through the data acquisition system for use by the microprocessor. These digitized signals may be analyzed in the time domain, frequency domain, through wavelet transforms and/or in other signal representation spaces.

Because a large number of pulse waveforms are acquired in the course of a single cardiac output measurement, it is preferable that waveforms be analyzed to extract significant parameters frequently, rather than storing all data and waiting until one or more full cuff inflation/deflation cycles are completed. These significant parameters include systolic pressure, diastolic pressure, pulse-pressure waveform characteristics, and the K1Ratio.

Assuming a pulse rate at about 60, desired accuracy of about 2 mm Hg (or ±5% FS for CO measurements), for blood pressure determinations over a range of 50–250 mm Hg, about 0.5 minutes and 32 k data samples stored in memory are required, without data compression or real time analysis. With real time signal analysis and intelligent cuff cycling, the full cuff inflation/deflation cycle and the data storage requirements may be further reduced, respectively, facilitating delayed processing. It is preferred to perform some degree of processing during sample acquisition. In addition to potentially reducing cycle time and data storage requirements, such analysis potentially allows a reading affected by a detected artifact to be repeated. In particular, the K1 and K3 signals may be obtained at any pressure above systolic and below diastolic pressure respectively, and therefore there is no need to obtain a full complement of readings at a full range of pressures. These signals may be statistically processed in order to improve the quality of the data.

DEVICE CONTROL

In order to perform the analysis of K1, the cuff is inflated to a level above systolic pressure, so that no Korotkoff sounds are evident. The actual pressure is not critical, but should not be so high as to cause pain or tissue damage, and therefore may be adaptively applied at a level of between about 150–300 mm Hg, based on a determined or predicted margin above systolic pressure, e.g., 20–30 mm Hg above systolic pressure.

For example, during cuff inflation, Korotkoff sounds may be heard up to an inflation pressure of 135 mm Hg. In order to ensure an adequate margin for securing a K1 signal, the cuff is inflated to about 20 mm Hg over the estimated systolic pressure, or to about 155 mm Hg. The cuff is held at this pressure with no inflation or deflation, for a series of beats while the signal is analyzed for the presence of artifacts. If it is likely that the data is unsuitable, an alarm condition is indicated to the operator of the device, and that portion of the data is ignored. The device may also continue to seek clean data for a limited period, although the cuff should be periodically deflated in order to prevent tissue ischemia and compartment syndrome.

After the cuff is inflated and K1 data obtained, the cuff is then slowly deflated, either continuously or stepwise, so that the cuff pressure changes between about 1–3 mm Hg between each successive heartbeat. When the cuff pressure drops below systolic pressure, Korotkoff sounds are heard. A portion of the wideband external pulse signal may be analyzed for both K1 and K2 as the cuff pressure drops.

Between systolic and diastolic pressures, the wideband external pulse data is analyzed for K2, which is somewhat related to Korotkoff sound analysis, but does not rely on audibility of the sounds. Rather, the K2 analysis determines the blood pressure corresponding to systole and diastole by analyzing the available data for characteristic corresponding signals, which, of course, include the audible signals received by the WEP transducer. Due to this broader data base, a more accurate assessment of systolic and diastolic blood pressures is possible, with reduced subjective influence. The K2 is characterized by a high frequency signal which appears, with cuff deflation, at systolic pressure and disappears at diastolic pressure. A computing system, e.g., a microcomputer, is provided to analyze the WEP signal for signal pattern characteristics in conjunction with a cuff pressure, and produces a set of BP readings, which may vary due to respiration, functional changes, or medical intervention. While the WEP is known for determining BP based on K2 analysis, the present invention provides an automated system having improved ease of use and performance. K2 analysis may also provide other clinical information, e.g., relating to auscultatory gaps. See, Cavallini et al., "Association of the Auscultatory gap with Vascular Disease in Hypertensive Patients", Ann. Intern. Med. 124:877–883 (1996), incorporated herein by reference.

Below the determined diastolic pressure, the K3 signal appears, which is a low frequency signal resembling the intraarterial pulse waveform. Obviously, components of this signal will repeat at the pulse rate, and further components will have a fundamental frequency at the respiration rate. Therefore, the low frequency response of the WEP transducer is particularly important in the analysis of this aspect of the WEP signal. A sensor system may be employed with a suitable composite frequency response across the required range, but in many cases, a single transducer provides a simpler and more inexpensive solution. Since the K2 signal reveals the absolute pressures of systole and diastole, the K3 signal may be calibrated. Mean arterial pressure, dp/dt and arterial compliance can then be determined.

While the K1 ratio is normally indicative of PVRI, e.g., by the formula:

$$K1R = -0.004 \times (PVRI) + 3.217$$

In certain instances, a more complex or alternate analysis may be preferred. For example, population subsets for which the above formula is somewhat inaccurate may be identified. Therefore, while the formula may be generally applicable, alternate analyses may be employed, e.g., by means of a lookup table, curve fitting algorithm or neural network. A neural network analysis may be used to extend the $K_1$ ratio analysis described above to the other aspects of the K1 signal, and indeed to other available data, which may include temperature, heart rate, EKG analysis, K2 analysis, K3 analysis, blood gas levels (preferably determined non-invasively, such as transcutaneous differential spectrophotometry), respiratory rate, subject's medical history, and other factors.

Thus, to analyze the WEP signal, the WEP transducer receives an acoustic signal, which is subject to electronic and digital signal filtering. Selected parameters are then analyzed, e.g., the heights of the first and second major peaks of the K1 waveform, as well as the height of the intervening trough, the time delay between the peaks and troughs of the K1 waveform, the first derivative of the K1 waveform at selected timepoints, as well as the subject's age, body surface area, the blood pressure as determined by K2 analysis, and parameters extracted from the K3 waveform. The BP, CO, PVR are then determined and output.

MULTITRANSDUCER SYSTEMS

An EKG interface to the system may be provided, and full vector cardiogram data may also be provided as an input to the system. This provides the possibility for integrated analysis, and also provides data by which to trigger an exception processing routine if an irregular heartbeat occurs during wideband external pulse analysis. Another alternative is to integrate the WEP monitor with a pulse oximeter. The WEP monitor may also be interfaced with a thoracic stethoscope or other transducer may be used to detect respiration, for correction of analysis or synchronization of data acquisition.

It is thus envisioned that WEP monitors may be used either as a stand alone monitor or in combination with other monitors. These other monitors may include a combination with one or more of EKG monitors, pulse onimeters, thoracic impedance monitors, fetal heart rate monitors; uterine contraction monitors, and comprehensive monitors, as a module and integrated into patient data acquisition systems e.g. Spacelabs, Hewlett Packard, Siemens, or Datex units. Since the WEP monitor has a cuff and specific WEP transducer, devices may be formed in a number of sizes, such as neonatal, pediatric, adult, extra large and geriatric. For each subpopulation, it may be necessary to provide a set of calibration coefficients, especially neonatal and pediatric.

U.S. Pat. Nos. 5,511,553, 5,307,818, 4,981,141, incorporated herein by reference relate to multiple physiological parameter monitoring devices. The present WEP analysis system may be advantageously integrated with such devices.

CLINICAL RELEVANCE

Monitoring Blood Pressure in Hypertensive Patients

In hypertensive patients, often systolic and diastolic pressure data alone is used to select treatment modality. However, with use of the WEP instrument according to the present invention, the additional knowledge of PVR will aid in diagnosis and choice of medication. For example, if the PVR is high, a vasodilator would be ideal. If the cardiac output was high and the PVR only slightly elevated, a beta blocker or calcium channel blocker may be appropriate. In hypertensives, monitoring the compliance of the arteries would help assess the long term benefit of treatment. Thus, the present technology becomes an invaluable adjunct to the isolated measurement of BP.

Home measurement of BP

It is becoming increasingly clear that measurement of BP by patients at home is a better way of identifying those patients who are truly hypertensive as opposed to those patients with so-called "white coat hypertension", a psychosomatic stress reaction to the traditional blood pressure measurement process. Home measurement of BP is also a better means of tracking BP and identifying a need for changes in medication. There are several limitations to this approach: Firstly, many patients have trouble taking their BP as they have trouble identifying the Korotkoff sounds and the measurements can be subjective. In addition, this technique does not provide for electronic recording and so the information cannot be entered in centralized data bases.

The present system therefore addresses this problem by automating the BP measurement process, as well as obtaining other data, such as CO, MAP and PVR. Home measurement of BP will be improved for the following reasons: Firstly, accurate measurements will be obtained and they are not subject to the errors of patient interpretation. Secondly, the information will be obtained electronically and so has the potential to be transmitted and entered into regional data bases via modems, etc. Finally, the added information provided by changes in PVR, CO, and dp/dt, etc. may provide physicians with additional information necessary to manage BP on a more rational basis. Management of BP in a home setting interfaced to national or regional centers may enable adjustment of treatment without regular visits to individual physicians, with resulting significant cost savings.

Therefore, one embodiment of the invention includes a memory for storing a plurality of sets of readings, optionally with the capacity to store raw data relating to putative artifacts or aberrant heartbeats. A telecommunication interface is provided, such as a 300-28.8K baud telephone modem, e.g., a v.34 modem PCMCIA (PC Card) interface device. Periodically, the device is connected to a telephone line, where it dials into a telecommunication center, and identifies and authenticates itself. The device then uploads the stored information, which includes the cardiovascular data, and optional exception data. If other monitors are integrated, such as EKG, pulse oximeter, pacemaker activity, or the like, the data from these may also be uploaded. After uploading, the data may be processed, and information downloaded to the user through the device. For example, a change in pharmaceutical prescription may be ordered, e.g., a change in dose or frequency. It is preferred that such prescription changes be analyzed and authorized by a licensed medical professional, so the telecommunication center may be staffed with trained individuals who verify any proposed automated changes, and possibly confer with the patient, as necessary, during the same telecommunication session with a voice over data or digital simultaneous voice and data (DSVD) modem.

Global Assessment of the Cardiovascular System

A free standing monitor providing heart rate (HR), BP, PVR, stroke volume (SV), CO, dp/dt and vascular compliance may be used as a screening device for cardiac health. As such, it may be broadly used during routine history and physical examinations by doctors or for assessing health risk by insurance companies. The free standing monitor may, in addition, be used to assess cardiovascular health in a variety of cardiovascular diseases, such as assessing the efficacy of treatment of heart failure or monitoring treatment with cholesterol lowering agents, etc.

Obstetrics Measurement of BP is routine in obstetrics in large part to assess the onset of preeclampsia. Preeclampsia is a microangiopathy characterized by an increased PVR. WEP monitoring will be able to assess the onset of preeclampsia early and thus can be a more accurate monitor than current modalities. See, Blank et al., "Systemic Vascular Tone in Normotensive and Hypertensive Pregnancies: Sequential Assessment with a New Noninvasive Technique", *Hypertension in Pregnancy* 12(2):224 (1993). Therefore, WEP recording as a part of home monitoring for obstetric patients could diagnose the onset of preeclampsia one or two weeks earlier than otherwise, allowing earlier treatment. The health care and economic implications of this are significant.

In labor, BP is measured repeatedly for a number of reasons, including assessment of preeclampsia. With aortocaval compression, cardiac output can decline but BP may still be preserved. WEP will be a more accurate monitor of circulatory status in obstetrics by detecting reduction of CO enabling optimal positioning of the mother. WEP monitoring may also be interfaced with fetal heart rate monitoring to provide an improved obstetric monitor.

Use in Hospitals Intensive Care, Emergency Room, and Operating Room Environments Currently, patients in intensive care type settings may have blood pressure, cardiac output, stroke volume and heart rate measured by a variety of noninvasive or invasive means. These technologies may be expensive and/or potentially dangerous to patients. For example, pulmonary artery catheters are associated with substantial risks including infection. Arterial pressure is often measured with arterial catheters. See, U.S. Pat. No. 5,509,424. Usually, these monitors are integrated with a variety of other modules into an integrated unit, such as BP, EKG, other pressures, pulse oximetry, cardiac output, temperature, etc. WEP monitoring may essentially replace existing BP monitoring. WEP monitoring provides a more accurate measure of SP, DP and MAP than existing noninvasive BP monitors. It also provides additional data (CO, SV, PVR, arterial compliance, and dp/dt). The WEP monitor may therefore be incorporated into existing monitors as a module, or as a separate instrument.

Assessment of Action of Medication

Many medications affect the circulation, causing symptoms of fainting, nausea and dizziness. Others may alter the PVR without affecting symptoms. Others may depress cardiac output. WEP can be used to monitor drug treatment and therefore may be used in clinical trials of drugs, to determine potential side effects as well as in the field where drugs are known to cause acute cardiovascular effects.

Monitor of Blood Loss or Dehydration

When blood is lost or dehydration occurs, the physiological response in humans is to constrict the arterioles (increase PVR) to maintain the BP. With conventional monitors, physicians cannot detect this early physiological response. With WEP, the increase in PVR will be measurable, so that appropriate treatment can be given early before shock occurs. For this reason, WEP will be a valuable monitor in emergency rooms, ambulances, operating rooms, post surgical care units and in obstetrics.

The monitoring of dehydration will also be useful for pediatric care, where vomiting and diarrhea are common and serious problems, and also in settings of fluid loss in hot environments e.g. sporting events, work environments, hyperthermia in summer, etc.

The system and method according to the present invention may be used in any mammal, although the details of the relations between the WEP signal and the cardiovascular function may vary. Thus, various animal research may be conducted using the present system and method, with the results then applied, e.g., to assist in the diagnosis or prognostic analysis of human disease.

Aid for Diagnosis of Acutely Ill Patient

The diagnosis of patients acutely ill with blood loss, sepsis, myocardial infarction, peritonitis, heart failure or pulmonary embolism may be aided using WEP monitoring by defining the relative disturbances in MAP, CO, PVR and HR.

Options for Presentation of Physiological Data

Because of the variety of data types, a versatile data presentation system may be useful for the interpretation of the observed data. The data can be presented as:

1. actual values determined, e.g., heart rate, SP, DP, MAP, dp/dt, K1R, upslope of K1, upslope of K3, time constant of decay of K3.
2. Derived values—PVRI, PVR, CO, SV, arterial compliance.
3. waveforms of K1, K2 and K3 can be displayed on a screen.
4. waveforms of K1, K2 and K3 can be printed out.
5. the data can be manipulated to aid in interpretation, e.g.:
   a) changes in compliance can be related to expected changes with age
   b) cardiac output can be reported as higher or lower than expected
   c) an inter-relationship between CO and PVRI can be developed to distinguish between volume depletion, early sepsis or a nonspecific hyperdynamic state.
   d) incorporation of dp/dt into this data may help identify the role of cardiac dysfunction in certain clinical settings. For example, it may be difficult to distinguish between cardiac depression and volume depletion in patients who have decreased CO in association with high PVR. WEP recording may facilitate the distinction.
   e) construct 3-D plot of CO vs. PVR vs. dp/dt to visually aid in diagnosis of changes.

OBJECTS OF THE INVENTION

It is therefore an object of the present invention to provide a system for assessing cardiovascular status non-invasively comprising an external peripheral pressure cuff, a wideband external pulse transducer, and a computing device for computing a peripheral vascular resistance.

It is a further object of the present invention to provide a method for estimating a K1 ratio comprising the steps of measuring a pressure waveform of a peripheral artery with blood flow occluded, measuring a difference in amplitude between a first major systolic peak and first major systolic trough, measuring an amplitude of a second major systolic peak and determining a ratio of a difference between said first major peak and said first major trough and said second major peak.

Another object of the present invention is to compute a peripheral vascular resistance based on a determined K1 ratio. A still further object according to the present invention is to compute a PVRI as a first order function of a K1R.

It is another object according to the present invention to provide a noninvasive cardiac monitoring system comprising a brachial artery cuff, a pressure control system for said cuff, a wideband acoustic transducer for measuring wideband acoustic emissions from the brachial artery, and a system for analyzing an output from the wideband acoustic transducer to produce data indicative of cardiac status.

It is a still further object according to the present invention to provide a metalized electro-acoustically sensitive polymer film as a wideband acoustic transducer for a cardiac status evaluating device.

By providing a low cost polymer film wideband acoustic external pulse transducer in conjunction with standard automated sphygmomanometer pneumatic controls, a system having enhanced functionality may be provided in cost effective manner.

For a full understanding of the present invention, reference should now be made to the following detailed description of the preferred embodiments of the invention as illustrated in the accompanying drawings.

BRIEF DESCRIPTION OF THE DRAWINGS

The detailed description of the preferred embodiments will be described with respect to the drawings, in which:

FIG. 1 is a tracing of a K1 signal;

FIG. 2 is a tracing of a K2 signal;

FIG. 3 is a tracing of a K3 signal;

FIG. 7 is a block diagram of an electronic circuit employing the segmented wideband external pulse transducer of FIG. 6;

DETAILED DESCRIPTION OF THE PREFERRED EMBODIMENTS OF THE INVENTION

Figure 4:
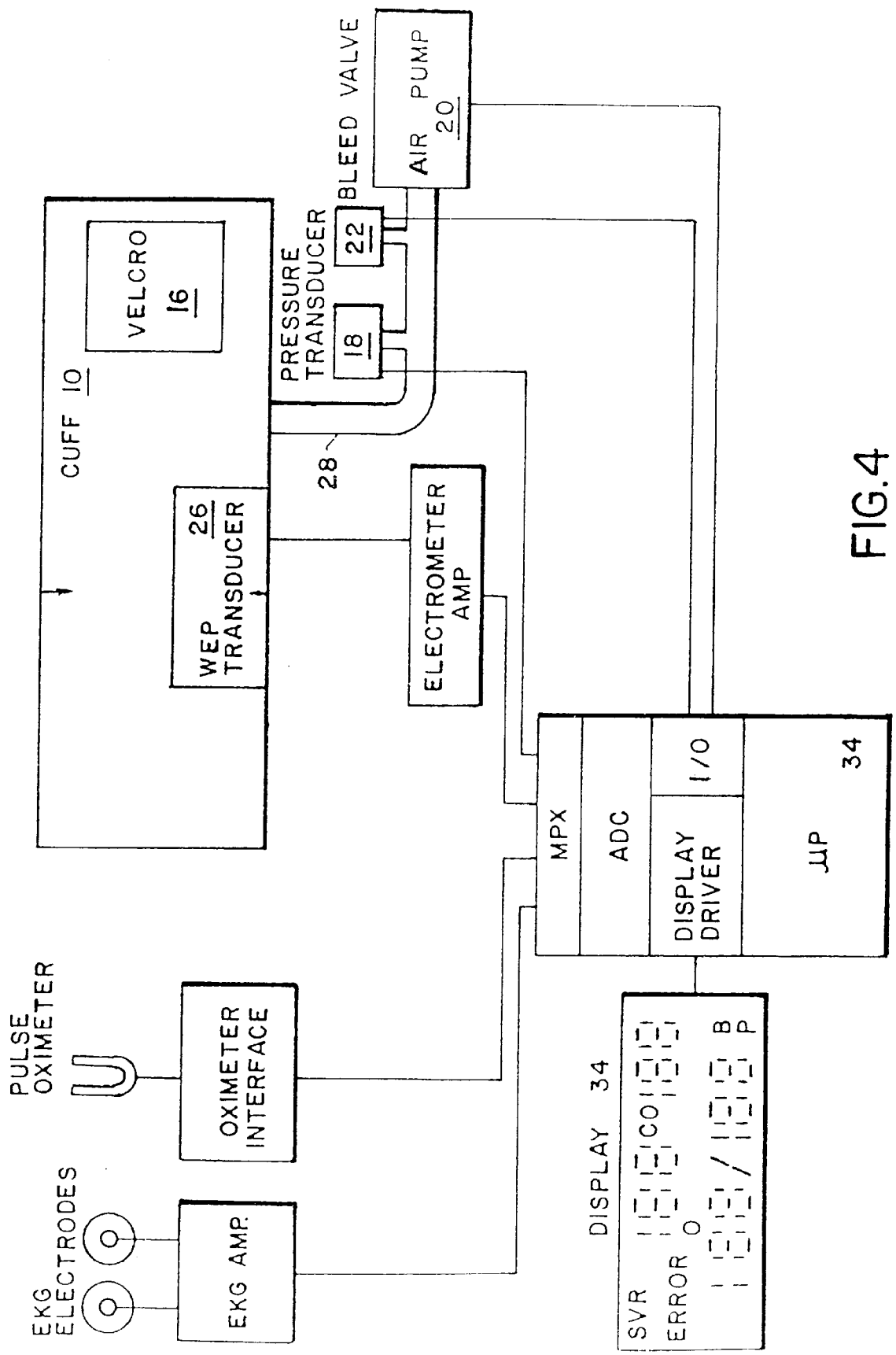
FIG. 4 is a block diagram of an electronic circuit according to the present invention.

The preferred embodiments and the best mode for practicing the present invention will now be described with reference to the Figures. Identical elements in the various figures have been assigned the same reference numerals.

Referring now to FIGS. 1–3, tracings of K1, K2 and K3 signals are shown, in both time domain and frequency domain, respectively. As can be seen, the K1 signal of FIG. 1 has a complex shape in both time and frequency domains, with a number of major peaks and troughs. FIG. 2 shows three different K2 waveforms, corresponding to Pc=SP, Pc<SP and Pc=DP, in both time domain and frequency domains. As noted in the time domain representations, a small trough (notch) is evident in the signal. The frequency domain representation reveals a rather evident high frequency peak, corresponding to this small trough in the time domain. FIG. 3 shows the K3 waveform, which is relatively smooth in the time domain with most of its energy at lower frequencies in the frequency domain representation.

EXAMPLE 1

FIG. 4 shows a schematic block diagram of an instrument incorporating the features of the present invention. A pressure cuff 10 for placement over the brachial artery 12 is provided having an inflatable bladder 14, Velcro® fastening system 16, a pressure transducer 18 and pump 20/bleed system 22. Between the skin 24 and cuff 10 is placed a wideband external pulse transducer 26 (at the distal end of the cuff) formed from a foil electret sensor (AT&T Bell Laboratories).

Figure 5A:
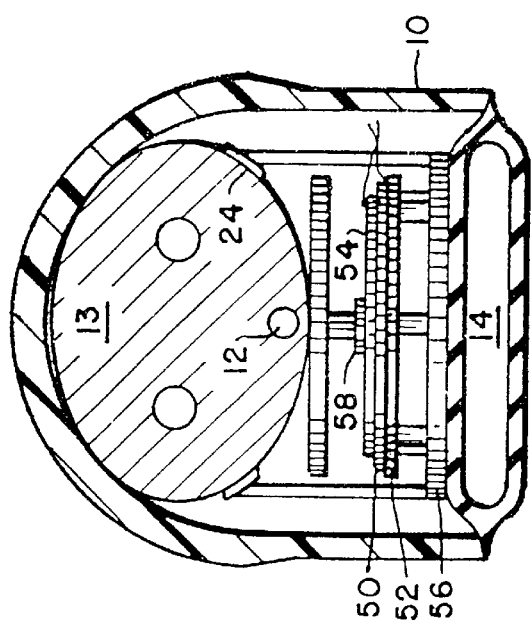
FIG. 5A is a perspective view of a brachial sphygmomanometer cuff having a wideband external pressure transducer according to the present invention.
Figure 5B:
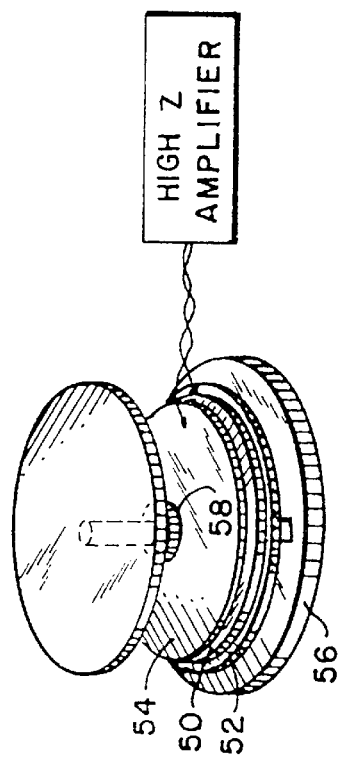
FIG. 5B is an exploded view of a wideband external pulse transducer.

Alternately, as shown in FIGS. 5A and 5B, a transducer may be formed from a piezoelectric element 50 mounted on a brass disk 52, with a surface electrode 54. The brass disk 52 is in turn mounted on a support 56, which tends to isolate the piezoelectric element 50 from the varying pressure of the cuff 10 and from vibrations. A probe 58 displaces the piezoelectric element 50 due to variations in arterial pressure in the artery 12.

The apparatus, as shown in FIG. 4, comprises a cuff 10 with embedded tubes which may be wrapped around the brachial artery 12 in the arm 13. Connected to the cuff 10 are pressurizing pump 20 and bleed system 22 to inflate and deflate the cuff 10 through the tube 28. A pressure transducer 18 is connected to the cuff 10 for detecting the cuff's pressure as it is inflated and deflated and for communicating the pressure data as an electrical signal to a microcontroller 32. Some pulse pressure data, such as the occurrence of Korotkoff sounds, may also be obtained from the cuff pressure transducer 18.

The operation of the measuring apparatus is coordinated by a microcontroller 32 which controls the pressurizing unit, an air pump 20, and the bleeding valve unit 22, a restricted flow solenoid valve. With the cuff 10 inflated to a pressure Pc by air pump 20, the artery 12 is squeezed by the cuffs pressure Pc. The pressure Pc in the cuff 10 is then deflated at nearly a constant bleeding rate through the bleeding valve unit 22. The wideband external pulse transducer 26 is held under the distal portion of the cuff 10, proximate to the brachial artery 12. This wideband external pulse transducer 26 is mounted to provide a relatively vibration free reference, so that the wideband transducer 26 output signal from the arterial system is easily analyzed. The pressure fluctuation of the pulsating blood flow starts to stretch the arterial wall which in turn causes a pressure fluctuation which is sensed by the wideband external pressure transducer 26.

The signal from wideband external pulse transducer 26 is coupled to an LMC6001 electrometer amplifier, for amplification and digitized by a 16 bit delta-sigma analog-to-digital converter (ADC). The output of the ADC is received by a microcontroller 32, which performs signal filtering and analysis.

The analyzed data is output though a visual display device 34 and a serial data port.

EXAMPLE 2

Figure 6:
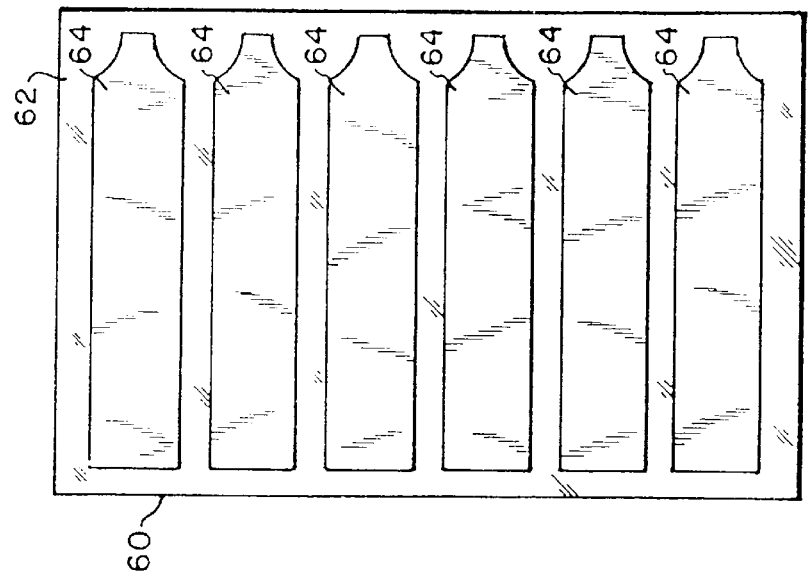
FIG. 6 is a top view of a segmented wideband external pulse transducer according to the present invention.

In order to optimize the signal-to-noise ratio and reduce artifacts, a multi-segmented wideband external pulse transducer 60 is provided as shown in FIG. 6. The multisegmented transducer is formed of a metalized polyvinylidene fluoride (PVDF) film 62, metalized with aluminum on both sides and etched with ferric chloride to form a segmented pattern 64 having strips approximately 0.25" wide and 1.5" long on one side. After metalization and connectorization, the transducer 60 may be conformally coated with an environmental sealant.

As shown in FIG. 7, a set of multiplexers is provided to feed buffered and amplified outputs from different segments strips. These multiple segments and multiplexers are provided to compensate for, inter alia, anatomical variations and difficulties in ensuring correct placement of the transducer over the brachial artery. After placement of the WEP and cuff over the artery, an optimal set of transducers is determined based on an analysis of the WEP transducer output.

While one segment may be optimal for receiving the brachial artery vibrations, another segment may be a useful control for compensating the output of the transducer segment.

The multiplexed electrometer amplifiers are fed to a digitizer circuit and the digitized information processed by a microcomputer. The microcomputer controls the multiplexer and processes the signals to select the single or two adjacent transducer segments which are best aligned to the brachial artery, based on the signal amplitude and freedom from interference. Outputs from these segments are selected through the multiplexer and digitized for processing by the microcomputer. The control segment may also read by the microcomputer.

The system shown in FIG. 7, for obtaining data from a multi-segmented wideband external pulse transducer 60 includes signal conditioning electronics 72, which include high impedance amplifiers for each segment and a multiplexer 74 for selectively interfacing an amplified signal with an analog to digital converter 76. A microprocessor 78 receives the digitized signals. The microprocessor controls the pump inflation and deflation through an interface 86, as described in example 1, and also receives a signal from a cuff pressure transducer 88 through the multiplexer 74.

The system includes an input from a keyboard 84 or keypad, and outputs to a display 82 and serial port 80.

Advantageously, additional inputs are provided to the system, such as pulse oximetry 88 and EKG 90 data, which are received by the microcomputer 78 through a data acquisition module 92.

The cuff pressure may be measured with, for example, a Sensym BP01 Blood Pressure Sensor (Sensym Inc., Milpitas, Calif.). This pressure sensor is provided in communication with the bladder of the pressure cuff, and has a pressure measurement range of about 0–300 mm Hg. The pressure signals are passed through a fluid, e.g., gas or liquid, to the pressure transducer. 8–12 bit analog to digital conversion of pressure sensor output is sufficient, with a sampling rate preferably of at least about 2 samples per second. The samples may be time-averaged to reduce noise effects, especially pulsation from the inflation pump. The samples may also be measured synchronously with an external event, such as pulse, inflation pump action. Or deflation valve action. The output of the analog to digital converter is processed by the microcomputer.

The computing system may be, for example, an IBM PC compatible system having an 80486, Pentium (P5 or 80586 class) or P6 (Pentium Pro) processor. A data acquisition board having high impedance signal conditioning and high resolution analog to digital conversion is provided as an ISA board, for example, a CyberResearch PZO 614 with a PZO TC10 Piezoelectric Signal Conditioning Module (10 sec. TC) and a PZO 1M 1 megabyte memory module (CyberResearch, Inc. Branford Conn.). Various software products may be used to perform the cuff inflation/deflation control and data analysis, including SnapMaster(™), Labtech Notebook for Windows v. 8.0 Control, or DASyLab+. The computer includes an SVGA display, keyboard, 2.0 GByte hard drive, 32 MBytes RAM, and runs Windows (Windows for Workgroups 3.11, Windows NT or Windows 95) operating System.

Figure 8:
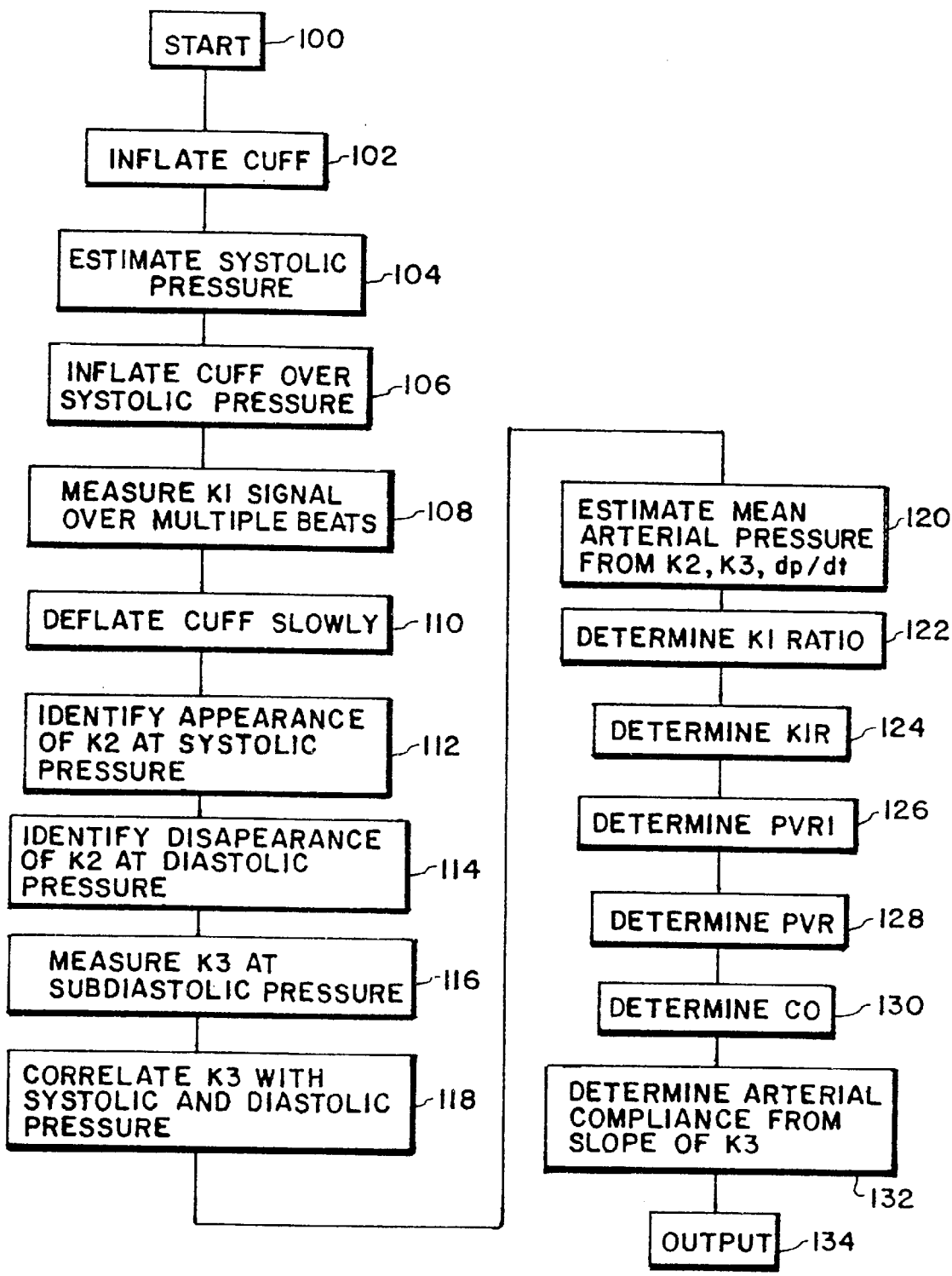
FIG. 8 is a flow diagram of a system for evaluating cardiac status using a pressure cuff and wideband external pulse transducer according to the present invention.
Figure 9A:
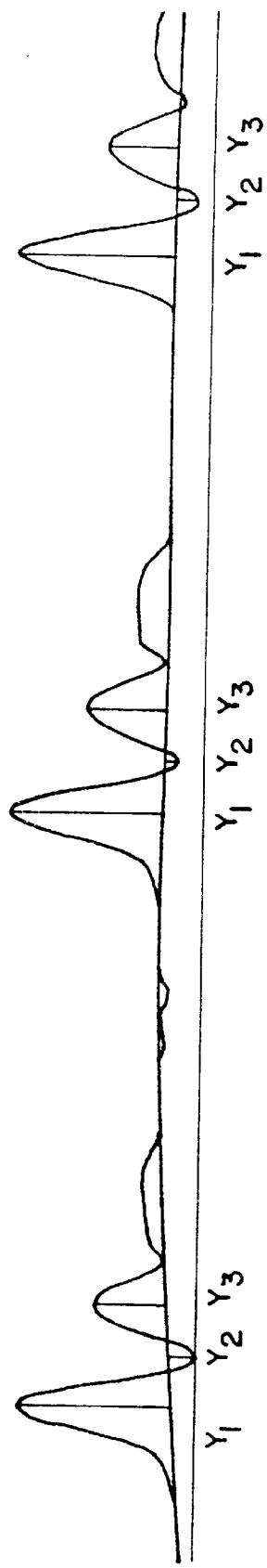
FIGS. 9A and 9B are comparative graphs of typical K1 patterns of young normotensive individuals and elderly hypertensive patients, respectively.
Figure 9B:
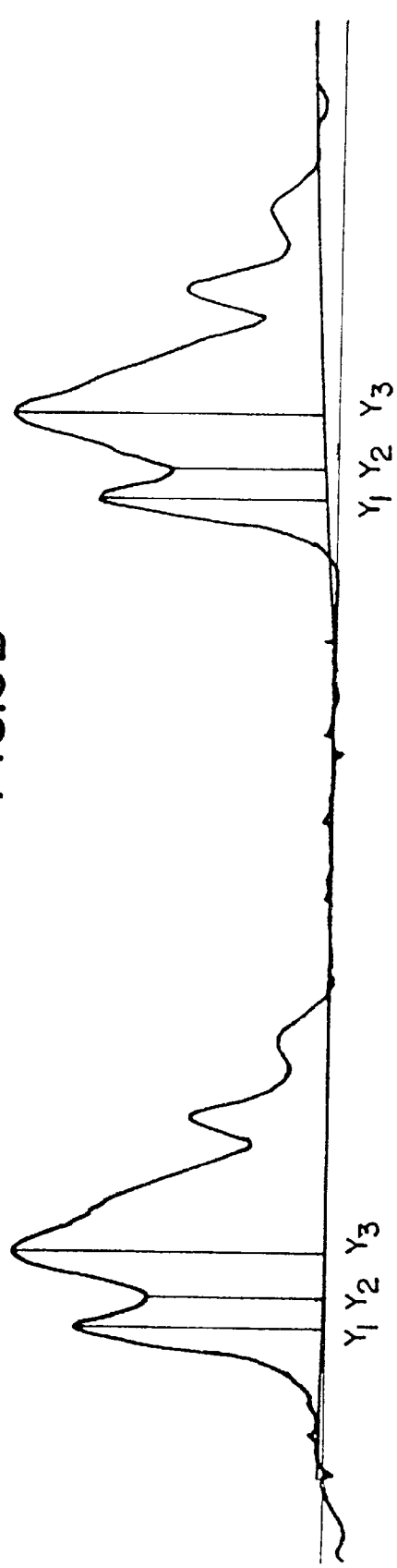

As shown in FIG. 8, a microcomputer first controls rapid inflation of the cuff 102 with an air pump. During inflation 102, the systolic blood pressure is estimated 104. This may be determined by K2 analysis from the WEP transducer or Korotkoff sound analysis from the pressure transducer. Cuff inflation proceeds to a pressure about 20–30 mm Hg above systolic pressure 106, as determined by the cuff pressure transducer, and at least to a point where blood flow is occluded, so that no Korotkoff sounds are evident. At this point, the cuff bladder is sealed, and a K1 signal analyzed 108. This signal is preferably analyzed in real time, and for sufficient period to measure an accurate and repeatable K1 ratio 122, as determined by the difference between the first major systolic peak and the first major systolic trough divided by the second major systolic peak. The K1 ratio is measured over a number of beats 108, with aberrant pulse waveforms eliminated and normal pulse waveforms subjected to statistical processing. The K1 data is acquired, for example, for a period of 5 to 6 seconds or 4 to 8 heartbeats.

The microcomputer then completes the analysis of the K1 data using an algorithm, which for example is a first order linear equation relating K1R and PVRI, peripheral vascular resistance indexed to body surface area. Alternately, the microcomputer may employ a lookup table, polynomial algorithm, more complex algorithm, artificial intelligence, fuzzy logic (semantic variable analysis) and/or neural network.

For example, a neural network may be trained to associate clinical data, e.g., diagnostic or prognostic data obtained from a population of mammals, e.g., patients, with WEP data. Thus, once trained, a set of inputs may be provided which will produce an output of one or more presumptive diagnoses or prognoses. In this manner, it is not necessary to explicitly define or understand the relationships between WEP data and clinical significance.

The cuff is then deflated 110 by opening the solenoid pressure bleed valve, such that the pressure drops at a rate which drops approximately 2–3 mm Hg. per heartbeat. The bleed may be at a fixed rate, through a restricted orifice, or through a proportionally controlled valve. When the cuff pressure is deflated to systolic pressure, a high frequency signal component is generated, i.e. K2, which is detected 112. As the cuff declines below diastolic pressure, the high frequency signal component disappears 114.

Below diastolic pressure, the wideband external pulse is measured, and a K3 pulse waveform determined 116. The peak of the K3 waveform is calibrated as systolic pressure, and the trough calibrated as the diastolic pressure 118, so that the mean arterial pressure (MAP) is determined 120.

The body surface area (or surrogate measurements) of the subject are derived or entered, e.g., via a keypad, and used to calculate peripheral vascular resistance 128 from the K1 ratio 122, through use of an algorithm by the microcomputer. This value may be entered prior to any BP determination, or as a correction factor after measurements are obtained. The cardiac output is then calculated 130 based on the PVR and MAP. Arterial compliance may also be determined from the slope of the K3 signal 132. Other data may be entered, e.g., age, and used for additional calculations. As stated above, specific presumptive diagnoses or EKG analyses may also be input to assist in the WEP analysis, although it is preferred that these added factors be optionally analyzed, so that these potential subjective biases are not integral to the basic cardiovascular status analysis.

In the case of long term monitoring of a subject, the absolute cardiac output may be less important in determining changes in cardiac status than changes in the K1, K2 and K3 waveforms themselves, or other derivative analyses. These changes may be monitored by standard logical analysis, neural networks or fuzzy logic systems, and need not be processed specifically to define cardiac output or systemic vascular resistance. For example, a neural network may be trained with data defining clinically significant changes of patients monitored with both invasive cardiac monitors and WEP monitors. An instrument so programmed (trained) may be useful for continuous monitoring of chronically ill patients, e.g., analyses taken every 5 minutes, instead of requiring an invasive cardiac monitor.

According to a preferred embodiment, the K1 signal is analyzed in the time-amplitude domain. The pressure amplitude of the first major peak, which corresponds to the initial systolic rise in pressure, is measured. The pressure amplitude of the first major trough, after the first major peak, is then subtracted from the amplitude of the first major peak. The pressure amplitude of the second major peak is then measured. The ratio of the two values is then determined. The natural logarithm of this dimensionless ratio is then determined to yield a value referred to as the "K1R", which has been found to have a relatively linear relationship to peripheral vascular resistance index:

$$K1R = -0.004 \times (PVRI) + 3.217.$$

The K1R and blood pressure are then used to estimate the cardiac output. The WEP system may be internally standardized using invasive cardiac output measurements of the same patient, where such data is available.

Because the WEP transducer is proximate to a single artery, from which it normally extrapolates systemic conditions throughout the organism, data relating to local conditions within the extremity may also be obtained. For example, local blood flow and arterial compliance may be determined.

EXAMPLE 3

A self-contained microcomputer board is provided for system control, data analysis and output. This board preferably includes a motor driver for an air pump for inflating the cuff, an electronically controllable bleed valve for deflating the cuff, a Sensym BP01 external blood pressure transducer for measuring the cuff pressure, an electrometer amplifier for interfacing the wideband external pulse transducer, e.g., a National Semiconductor LMC6001 (or other suitable LMC6XX or LMC6XXX series amplifier) or Analog Devices AD549. The inputs of the pressure transducer and wideband external pulse transducer may be further subjected to band limiting filtering. A National Semiconductor LM12458 Data Acquisition System (12 bit plus sign) device is provided for analog interfacing to the WEP transducer, pressure transducer, and the other transducers.

During cuff inflation, an automatic amplitude calibration routine is be used to linearize the wideband external pulse transducer system for changes in output due to load pressure. Therefore, as cuff pressure varies at subdiastolic pressure or supersystolic pressures, the cuff pressure versus output amplitude function is characterized and the results used to compensate other readings. This calibration step allows the use of nonlinear transducer elements and those configurations which produce output variations with changes in loading pressure.

A simple 2 lead (plus ground) EKG data input is provided to the data acquisition system, and processed in conjunction with the cardiac output data. The EKG data is used for synchronization of WEP processing and the detection of aberrant heartbeats, for possible exception processing.

A peripheral pulse oximeter probe, e.g., a photoelectric finger probe, is also provided as an input to the microprocessor, used as a failsafe device to prevent peripheral ischemia due to pressure cuff operation. A thoracic stethoscope or other transducer may be used to detect respiratory activity, for correction of analysis or synchronization of data acquisition.

It should be understood that the data acquired by the various sensors may be analyzed in various manners to produce clinically useful data, and that therefore the wideband external pulse transducer system may form the basis of many different types of instruments, especially of noninvasive types.

Having illustrated and described the principles of the invention in a preferred embodiment, it should be apparent to those skilled in the art that the invention can be modified in arrangement and detail without departing from such principles. For example, discrete or integrated components of various types may be employed for the various parts of the apparatus, as is known to those of skill in the art. Features of the invention shown in software may also be implemented in hardware.

What is claimed is:

1. An apparatus for assessing cardiovascular status of a mammal comprising:
   a system for locally applying a pressure to an artery, capable of restricting blood flow through said artery;
   a wideband external pulse transducer, having an output, situated to measure acoustic signals proximate to said artery; and
   a computing device receiving said output for calculating based on said output measured during a period of completely occluded flow through said artery, a peripheral vascular impedance value.

2. The apparatus according to claim 1, wherein said value is a peripheral vascular resistance.

3. The apparatus according to claim 1, said computing device further calculating a peripheral vascular resistance based on said value and a biometric factor relating to the mammal.

4. The apparatus according to claim 3, wherein said biometric factor relates to a body surface area of the mammal.

5. The apparatus according to claim 3, wherein said biometric factor relates to a size of a vascular tree of the mammal.

6. The apparatus according to claim 1, wherein said computing device analyzes a temporal amplitude pattern of said output.

7. The apparatus according to claim 6, wherein said system for locally applying a pressure to an artery occludes said artery, said temporal amplitude pattern comprising a pair of adjacent amplitude peaks and an intervening dip, the computing device calculating a ratio of the amplitude difference of first peak and intervening dip, and the second peak.

8. The apparatus according to claim 7, wherein the computing device calculates said value as a linear first order function of the natural logarithm of said ratio.

9. The apparatus according to claim 8, wherein the value corresponds to the peripheral vascular resistance indexed for body surface area, said linear first order function approximating 714 mm Hg dyne sec $cm^{-5}$ $m^{-2}$ minus 250 times a natural logarithm of said ratio.

10. The apparatus according to claim 9, wherein said computing device further calculates a peripheral vascular resistance by correcting for body surface area.

11. The apparatus according to claim 1, wherein said value varies with peripheral vascular resistance and body surface area.

12. The apparatus according to claim 1, wherein said system for locally applying a pressure to an artery has at least two states, a first state in which said artery is occluded and a second state in which arterial blood flow is partially occluded.

13. The apparatus according to claim 12, wherein said computing device controls a state of said system for locally occluding arterial blood flow.

14. The apparatus according to claim 12, wherein said computing device determines a blood pressure based on said output and a state of said system for locally applying a pressure to an artery.

15. The apparatus according to claim 14, wherein said blood pressure is determined as a systolic and a diastolic pressure.

16. The apparatus according to claim 12, wherein said system for locally applying a pressure to an artery has a third state which does not occlude arterial blood flow, said computing device determining an arterial pulse pressure waveform based on said output.

17. The apparatus according to claim 16, wherein said computing device calculates a mean arterial pressure based on said arterial pulse pressure waveform.

18. The apparatus according to claim 17, wherein said computing device calculates a value relating to cardiac output based on said mean arterial pressure and said value.

19. The apparatus according to claim 18, wherein said computing device calculates a heart rate and value relating to stroke volume from said heart rate and said cardiac output.

20. The apparatus according to claim 16, wherein said output, when said system for locally occluding arterial blood flow is in said non-occlusive state, is analyzed by said computing device to determine a value relating to arterial compliance.

21. The apparatus according to claim 20, wherein said computing device compensates said peripheral vascular impedance value for body surface area.

22. The apparatus according to claim 21, wherein said output has a downsloping amplitude period, said value relating to said arterial compliance being determined as an exponential timeconstant of said downsloping amplitude period divided by said peripheral vascular impedance value compensated for body surface area.

23. The apparatus according to claim 1, wherein said computing device further calculates a mean arterial blood pressure compensated for arterial pulse pressure waveform.

24. The apparatus according to claim 1, wherein said computing device analyzes said output to determine a change in arterial pressure over time.

25. The apparatus according to claim 24, wherein said computing device determines a value relating to cardiac contractility from said change in arterial pressure over time.

26. The apparatus according to claim 1 wherein said wideband external pulse transducer comprises a foil electret transducer.

27. The apparatus according to claim 1 wherein said wideband external pulse transducer comprises a metalized polyvinylidene fluoride polymer film.

28. A method for determining a peripheral vascular impedance of a mammal, comprising the steps of:
   measuring a WEP waveform of a peripheral artery with blood flow occluded;
   measuring a difference in amplitude between a first major systolic peak and first major systolic trough and measuring an amplitude of a second major systolic peak;
   determining a ratio of a difference between said first major peak and said first major trough and said second major peak; and
   determining, based on the determined ratio, a peripheral vascular impedance.

29. The method according to claim 28, further comprising the step of determining a biometric factor of the mammal, and compensating the peripheral vascular impedance to determine a peripheral vascular resistance.

30. The method according to claim 29, wherein the biometric factor is body surface area.

31. The method according to claim 28 further comprising the step of determining an intraarterial pressure waveform by measuring a wideband external pressure waveform over a peripheral artery with a blood flow therethrough not occluded and calibrating said determined waveform with a maximum systolic and minimum diastolic pressures as determined by partial occlusion with an externally applied pressure.

32. The method according to claim 31, further comprising the step of determining a cardiac output based on the intraarterial waveform and the peripheral vascular impedance.

33. A noninvasive cardiac monitoring apparatus comprising:
   a brachial artery cuff;
   pressure control system for controlling a pressure in said cuff;
   a wideband acoustic transducer, having an output, for measuring acoustic emission proximate to said cuff, and
   a system for analyzing said output at least during a period of complete occlusion of flow in the brachial artery due to pressurization of said cuff, to determine peripheral vascular impedance.

34. The apparatus according to claim 33, further comprising a system for determining a mean arterial pressure from said output.

35. The apparatus according to claim 34, further comprising a system for calculating cardiac output.

36. The system according to claim 33 wherein said acoustic transducer comprises a metalized electret polyvinylidene fluoride polymer film.

37. The apparatus according to claim 33, wherein said analyzing system comprises means for determining a peripheral vascular impedance based on said output while said cuff is held at a supersystolic pressure.

38. The apparatus according to claim 37, wherein said analyzing system comprises means for:
   measuring a WEP waveform of a peripheral artery with blood flow occluded; and
   measuring a ratio of a difference in amplitude between a first major systolic peak and first major systolic trough and an amplitude of a second major systolic peak.

39. The apparatus according to claim 38, wherein said estimating means analyzes a first order linear equation relating a natural logarithm of the determined ratio and the peripheral vascular resistance indexed for body surface area.

40. The apparatus according to claim 33, further comprising means for determining mean arterial pressure.

41. The apparatus according to claim 33, further comprising means for determining cardiac output.

42. A method for assessing cardiovascular status of a mammal comprising:
   providing a system for locally applying a pressure to an artery, capable of restricting blood flow through said artery;
   providing a wideband external pulse transducer, having an output, situated to measure acoustic signals proximate to said artery; and
   analyzing the output of the wideband external pulse transducer, at least during a period of complete arterial occlusion, for the mammal based on a derived relation between diagnostic or prognostic clinical data and wideband external pulse transducer data for a population of mammals.

43. The method according to claim 42, wherein said derived relation comprises an artificial neural network.

44. The method according to claim 42, wherein said derived relation comprises a polynomial algorithm relating characteristics of the wideband external pulse transducer output with a diagnostic or prognostic clinical data value.

45. The method according to claim 42, wherein said analysis of the derived relation determines a likely diagnosis or prognosis of the mammal.

46. The method according to claim 42, wherein said analyzing step includes the substep of calculating, based on the output of the wideband external pulse transducer, a peripheral vascular impedance value.

47. The method according to claim 42, wherein said analysis of the derived relation estimates a blood flow through an artery proximate to the wideband external pulse transducer.

48. The method according to claim 42, wherein said analysis of the derived relation estimates a compliance of an artery proximate to the wideband external pulse transducer.

49. The method according to claim 42, wherein said analysis of the derived relation includes analysis of wideband external pulse transducer data obtained while arterial blood flow proximate to the transducer is partially occluded.

50. The method according to claim 42, wherein said analysis of the derived relation includes analysis of wideband external pulse transducer data obtained while arterial blood flow proximate to the transducer is occluded.

51. An apparatus for assessing cardiovascular status of a mammal comprising:
   a system for selectively and completely occluding blood flow through a peripheral artery;
   a wideband external pulse transducer, having an output, situated to measure acoustic signals proximate to said artery; and
   a processor, for estimating, based on said output, a cardiovascular organ tone.

52. The apparatus according to claim 51, wherein said cardiovascular organ tone comprises cardiac contractility.

53. The apparatus according to claim 51, wherein said processor estimates the cardiovascular organ tone of the mammal, based on said output over a plurality of pulse cycles and a plurality of differing degrees of arterial restriction.

54. The apparatus according to claim 53, wherein said cardiovascular organ tone comprises a peripheral vascular impedance.

55. A method for assessing a cardiovascular status of a mammal, comprising the steps of:
   providing data relating to a predetermined relationship of cardiovascular status with a set of pulse waveform amplitudes at at least three distinct pulse phases, corresponding to characteristic points of the pulse waveform, of a peripheral artery at a position proximate to a selectively controlled restriction of flow through the peripheral artery, for a population of mammals of the same species, the predetermined relationship comprising a mathematical function, having as a parameter a ratio of two different mathematical functions of at least one of the pulse waveform amplitudes;
   measuring, during the distinct pulse phases, waveform amplitudes of a peripheral artery of a member of the species of mammal at a position proximate to a selectively controlled restriction of flow through the artery;
   determining, according to the predetermined relationship, the cardiovascular status of the member of the species of mammal.

56. The method according to claim 55, wherein said mathematical function, has as a parameter a ratio of an amplitude difference between two peaks and a trough in the pulse waveform.

57. The method according to claim 55, wherein the pulse waveform is measured non-invasively and the restriction of flow through said peripheral artery is caused by a selectively applied external compression, the mathematical function defining the predetermined relationship further comprising a surface area of the member of the species of the mammal and measured pulse waveforms under at least two different degrees of arterial compression.

* * * * *